US011116862B2

(12) United States Patent
Xie

(10) Patent No.: US 11,116,862 B2
(45) Date of Patent: Sep. 14, 2021

(54) DEVICES AND METHODS FOR SELECTIVELY PROVIDING AN ODOR-RICH ENVIRONMENT

(71) Applicant: THE GENERAL HOSPITAL CORPORATION, Boston, MA (US)

(72) Inventor: Zhongcong Xie, Andover, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 265 days.

(21) Appl. No.: 16/082,853

(22) PCT Filed: Mar. 8, 2017

(86) PCT No.: PCT/US2017/021422
§ 371 (c)(1),
(2) Date: Sep. 6, 2018

(87) PCT Pub. No.: WO2017/156167
PCT Pub. Date: Sep. 14, 2017

(65) Prior Publication Data
US 2020/0289696 A1 Sep. 17, 2020

Related U.S. Application Data

(60) Provisional application No. 62/305,139, filed on Mar. 8, 2016.

(51) Int. Cl.
*A61L 9/12* (2006.01)
(52) U.S. Cl.
CPC .............. *A61L 9/125* (2013.01); *A61L 9/122* (2013.01); *A61L 2209/11* (2013.01); *A61L 2209/12* (2013.01); *A61L 2209/13* (2013.01)

(58) Field of Classification Search
None
See application file for complete search history.

(56) References Cited

U.S. PATENT DOCUMENTS 4,116,329 A    9/1978 Garden
5,023,020 A    6/1991 Machida
(Continued)

OTHER PUBLICATIONS

Hunt et al. Aromatherapy as Treatment for Postoperative Nausea: A Randomized Trial. Anesthesia & Analgesia, vol. 117, No. 3, pp. 597-604. https://journals.lww.com/anesthesia-analgesia/fulltext/2013/09000/aromatherapy_as_treatment_for_postoperative.10.aspx (Year: 2013).*

(Continued)

*Primary Examiner* — Jelitza M Perez
(74) *Attorney, Agent, or Firm* — Nixon Peabody LLP

(57) ABSTRACT

A device for selectively providing an odor-rich environment includes a housing and a cover. The housing includes a central cavity and a plurality of chambers configured to store a predefined fragrance therein and having a respective outlet formed on an outer wall of the housing. The cover includes an exterior surface having at least one vent formed on the exterior surface. The exterior surface includes an interior sidewall and an exterior sidewall forming an inner chamber that slidably engages the housing such that the cover is configured to move between an open position and a closed position. Responsive to the cover being in the open position, the at least one vent is generally adjacent to the outlet of at least one of the plurality of chambers of the housing. The odor-rich environment can assist in preventing and/or treating postoperative delirium (POD) postoperative cognitive dysfunction (POCD), and/or pain in a subject.

18 Claims, 14 Drawing Sheets

(56) References Cited

U.S. PATENT DOCUMENTS

| | | | |
|---|---|---|---|
| 5,610,674 A * | 3/1997 | Martin | B01F 3/022 352/85 |
| 6,713,024 B1 | 3/2004 | Arnell | |
| 2006/0039835 A1 | 2/2006 | Nottingham | |
| 2008/0000930 A1 | 1/2008 | Alticosalian | |

OTHER PUBLICATIONS

Fayazi et al. The Effect of Inhalation Aromatherapy on Anxiety Level of the Patients in Preoperative Period. Iranian Journal of Nursery and Midwifery Research. vol. 16(4). pp. 1-8 https://www.ncbi.nlm.nih.gov/pmc/articles/PMC3583096/ (Year: 2011).*

Fayazi et al.; "The effect of inhalation aromatherapy on anxiety level of the patients in preoperative period"; 2011; retrieved from the Internet on Jan. 5, 2017 from: <URL=https://www.ncbi.nlm.nih.gov/pmc/articles/PMC3583096/> (5 pages).

Hunt et al.; "Aromatherapy as Treatment for Postoperative Nausea: A Randomized Trial"; Anesthesia & Analgesia, vol. 117, No. 3, pp. 597-604; Sep. 2013; retrieved from the Internet from: <URL=http://journals.1ww.com/anesthesia-analgesia/Fulltext/2013/09000/Aromatherapy_as_Treatment_for_Postoperative.10.aspx> (8 pages).

International Search Report and Written Opinion of International Searching Authority, PCT/US2017/021422, dated May 25, 2017 (9 pages).

* cited by examiner

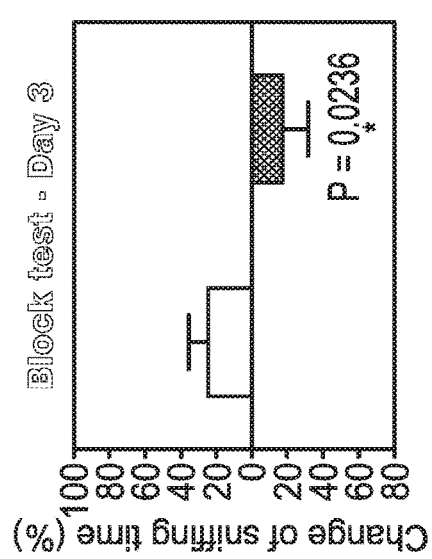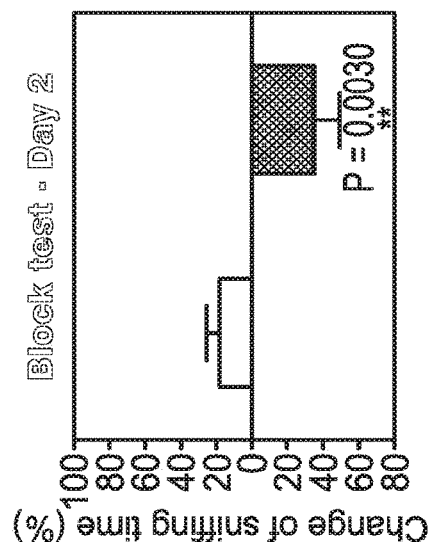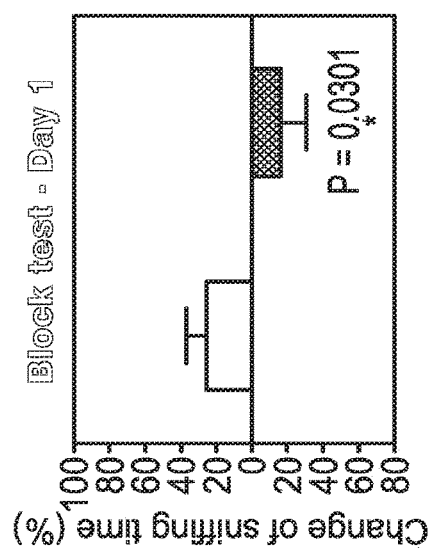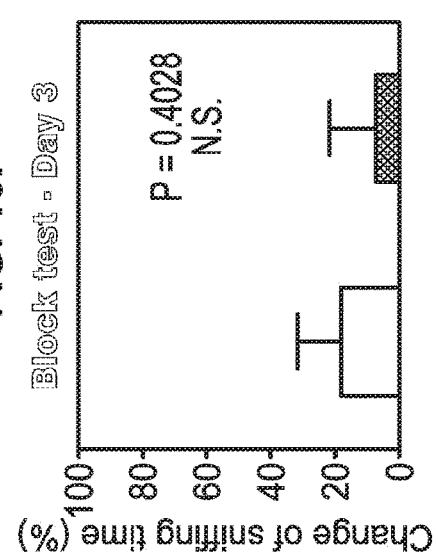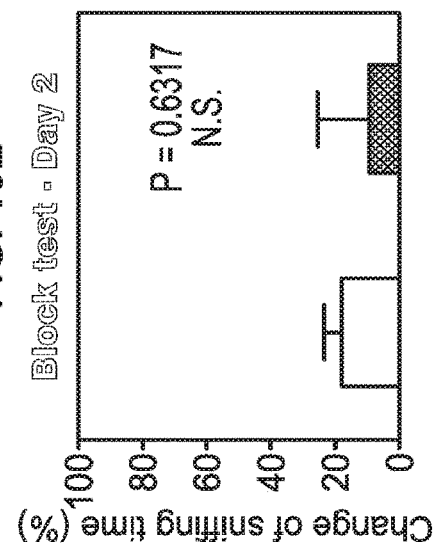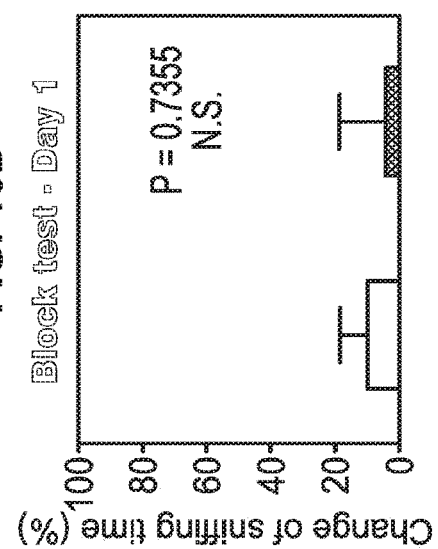

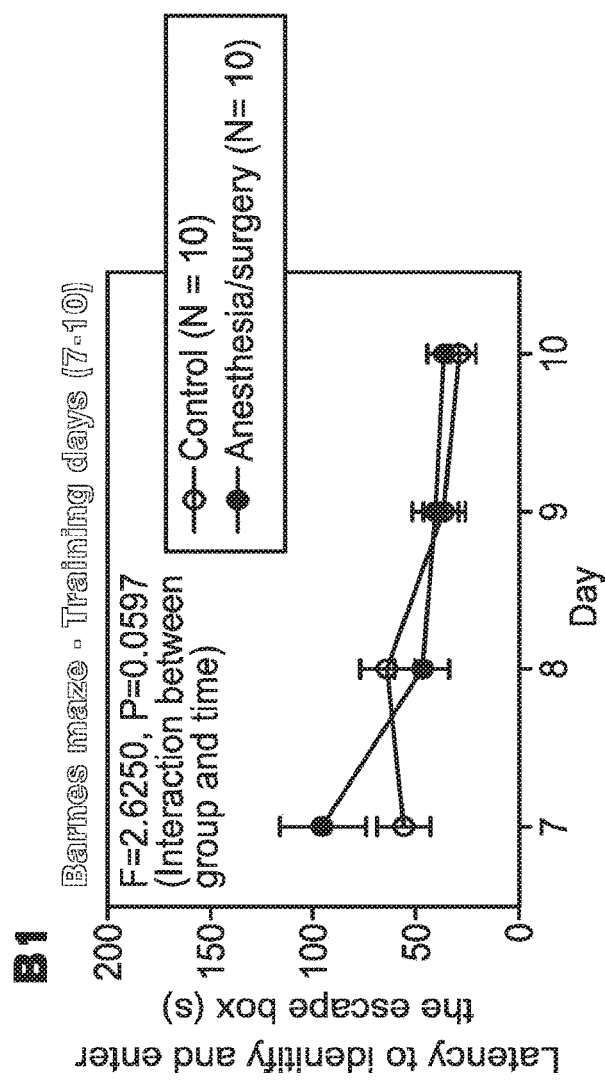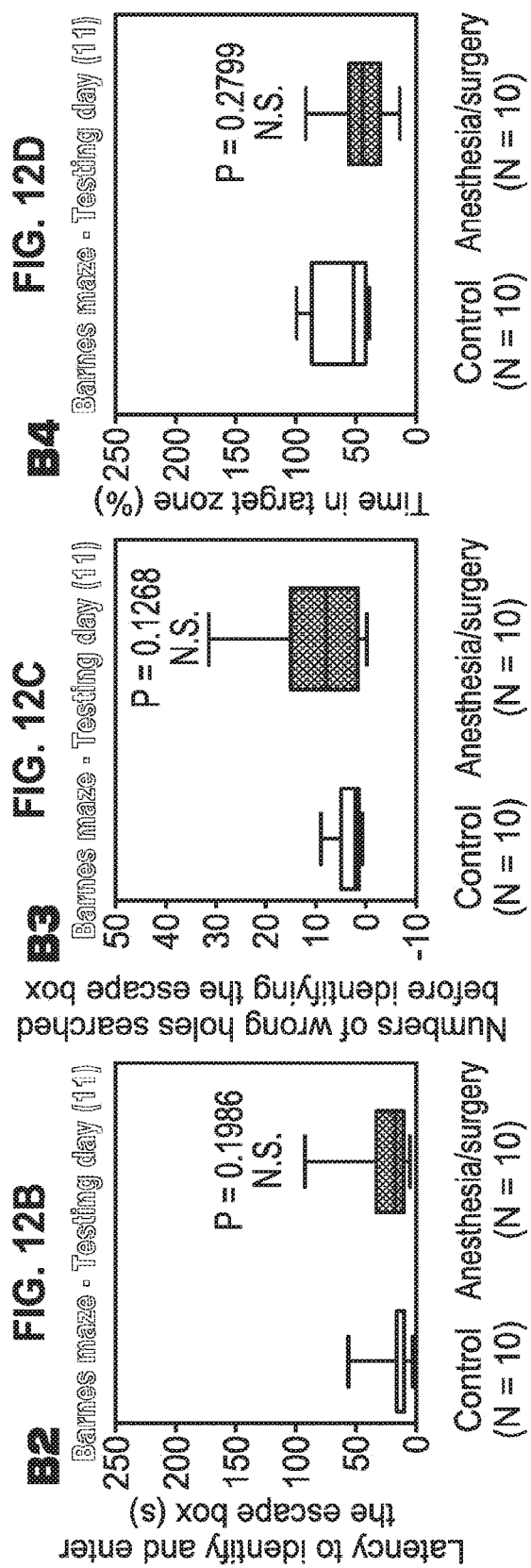
FIG. 12A
FIG. 12B
FIG. 12C
FIG. 12D

DEVICES AND METHODS FOR SELECTIVELY PROVIDING AN ODOR-RICH ENVIRONMENT

CROSS-REFERENCE TO RELATED APPLICATION

This application is a U.S. National Stage of International Application No. PCT/US2017/021422, filed Mar. 8, 2017, which claims priority to and the benefit of U.S. Provisional Application No. 62/305,139, filed on Mar. 8, 2016, each of which is hereby incorporated by reference herein in its entirety.

GOVERNMENT RIGHTS

This invention was made with government support under by Grant Nos. R01GM088801, R01AG041274, and R01HD 086977 from National Institutes of Health, Bethesda, Md. The United States Government has certain rights in the invention.

TECHNICAL FIELD

The present disclosure relates generally to selectively providing an odor-rich environment and, more particularly, to devices and methods for selectively providing an odor-rich environment for assisting in preventing and/or treating postoperative delirium and/or postoperative cognitive dysfunction, and pain.

BACKGROUND

Postoperative delirium ("POD") and postoperative cognitive dysfunction ("POCD")—common post-operative complications—have become an important clinical consideration in the field of geriatric medicine. The pathogenesis of POD and POCD and targeted interventions, effective treatment, and prevention regimens are still largely unknown. POCD and POD are associated with postoperative pain.

Delirium, an acute, transient, fluctuating disturbance in attention, cognition and consciousness level, is associated with short- and long-term mortality and morbidity, dementia, and deterioration in quality of life. POD is a common postoperative complication, occurring in as many as about 15-53% of postoperative patients, and can lead to an about 2-20 fold increase in mortality, long term functional impairment, postoperative cognitive dysfunction, and/or costs of medical care.

Of the more than 260 million patients who have surgeries each year worldwide, it is estimated that one to two million individuals over the age of 65 may suffer from POCD each year in the United States alone.

Further, it is estimated that the healthcare costs associated with delirium alone are more than $162 billion per year in the United States. As the population of older surgical patients continues to grow, it is expected that there will be an increase in cases of POD and POCD. Moreover, recent studies have shown that children who undergo anesthesia and surgery at an early age may have an increased risk for developed POD and/or POCD. At the present time, there is no meaningful prevention or treatment for POD and POCD. Thus, new devices and methods are needed for preventing and/or treating POD and POCD. The present disclosure is directed towards addressing these and other problems.

SUMMARY

According to some implementations of the present disclosure, a device for selectively providing an odor-rich environment comprises a housing and a cover. The housing includes a central cavity and a plurality of chambers arranged around the periphery of the central cavity. Each of the plurality of chambers is configured to store one or more predefined fragrance therein and has a respective outlet formed on an outer wall of the housing. The cover includes an exterior surface having a top portion and an exterior sidewall, the cover further including at least one interior sidewall, the at least one exterior sidewall and at least one interior side wall forming an outer chamber therebetween. The at least one interior sidewall forms a generally central inner chamber therebetween. The cover also includes at least one vent formed on the exterior surface. The outer chamber is configured to slidably engage the housing such that the cover is configured to move between an open position and a closed position. Responsive to the cover being in the open position, the at least one vent is generally adjacent to the outlet of at least one of the plurality of chambers of the housing. Responsive to the cover being in the closed position, the exterior surface of the housing is generally adjacent to the respective outlet of at least one of the plurality of chambers of the housing.

According to some implementations of the present disclosure, a method for selectively providing an odor rich environment includes providing a device. The device includes a housing and a cover. The housing includes a central cavity and a plurality of chambers arranged around the periphery of the central cavity. Each of the plurality of chambers has a respective outlet formed on an outer wall of the housing. At least one fragrance is housed within at least one of the plurality of chambers of the housing. The cover includes an exterior surface having a top portion, an exterior sidewall, and at least one interior sidewall. The exterior sidewall and the interior side wall forming an outer chamber therebetween. The interior sidewall forms a generally central inner chamber therebetween. The cover further includes at least one vent formed on the exterior surface. The outer chamber is configured to slidably engage the housing. The cover is moved to an open position such that the at least one vent is generally adjacent to the respective outlet of at least one of the plurality of chambers of the housing, thereby causing the at least one fragrance of at least one of the plurality of chambers to be emitted through the at least one vent and at least one respective outlet.

According to some implementations of the present disclosure, a method for reducing or preventing postoperative delirium, postoperative cognitive dysfunction, and pain of a subject includes administering an odor-rich environment comprising one or more preselected fragrances to the subject prior to and after the subject being administered anesthesia. This odor-rich environment can be combined with displaying pictures, virtual reality scenery, videos, and/or brain stimulation games to challenge brain function.

These and other aspects of the present invention will become more apparent from the following detailed description of the device and methods in conjunction with the accompanying drawings.

BRIEF DESCRIPTION OF THE DRAWINGS

The accompanying drawings, which are incorporated into this specification, illustrate one or more exemplary embodiments of the inventions and, together with the detailed description, serve to explain the principles and applications of these inventions. The drawings and detailed description are illustrative and are intended to facilitate an understanding of the inventions and their application without limiting the scope of the inventions. The illustrative embodiments can be modified and adapted without departing from the spirit and scope of the inventions.

FIGS. 10A-10F depicts a series of experimental results for a block test for a control study and an interventional study according to some aspects of the present disclosure;

FIG. 12A is a graph of experimental results for a Barnes maze test for an interventional study according to some aspects of the present disclosure;

FIG. 12B is a graph of experimental results for the Barnes maze test of FIG. 12A;

FIG. 12C is another graph of experimental results for the Barnes maze test of FIG. 12A;

FIG. 12D is yet another graph of experimental results for the Barnes maze test of FIG. 12A.

Figure 1:
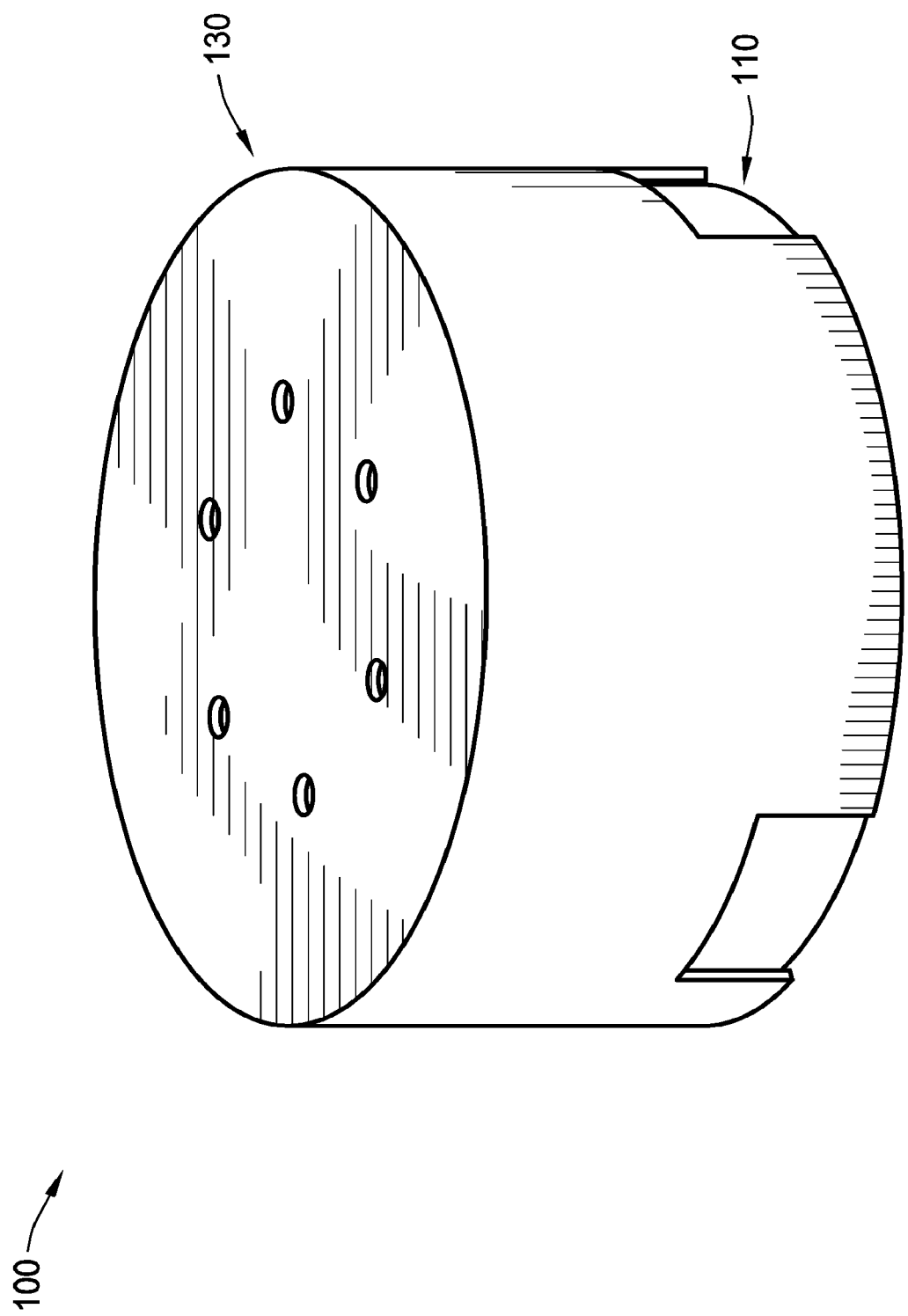
FIG. 1 is a perspective view of a device for selectively providing an odor-rich environment according to implementations of the present disclosure.

The present disclosure is susceptible to various modifications and alternative forms, and some representative embodiments have been shown by way of example in the drawings and will be described in detail herein. It should be understood, however, that the inventive aspects of the disclosure are not limited to the particular forms disclosed. Rather, the disclosure is to cover all modifications, equivalents, and alternatives falling within the spirit and scope of the invention as defined by the appended claims.

DETAILED DESCRIPTION

The devices and methods described herein have been shown to create an enriched environment that may attenuate anesthesia/surgery-induced cognitive impairment, delirium, and pain. Preliminary data has surprisingly shown that stimulation of a patient's olfactory function by smelling a different scent(s) attenuates the cognitive impairment induced by surgery under anesthesia in laboratory animals. The preliminary data has also shown that providing an enriched environment can reduce a postoperative patient's pain. The devices and methods described herein are directed to providing an enriched environment for providing these and other therapeutic and/or prognostic benefits in association with personalized medical prevention and treatment, e.g., for POD, POCD, and/or pain.

Figure 2:
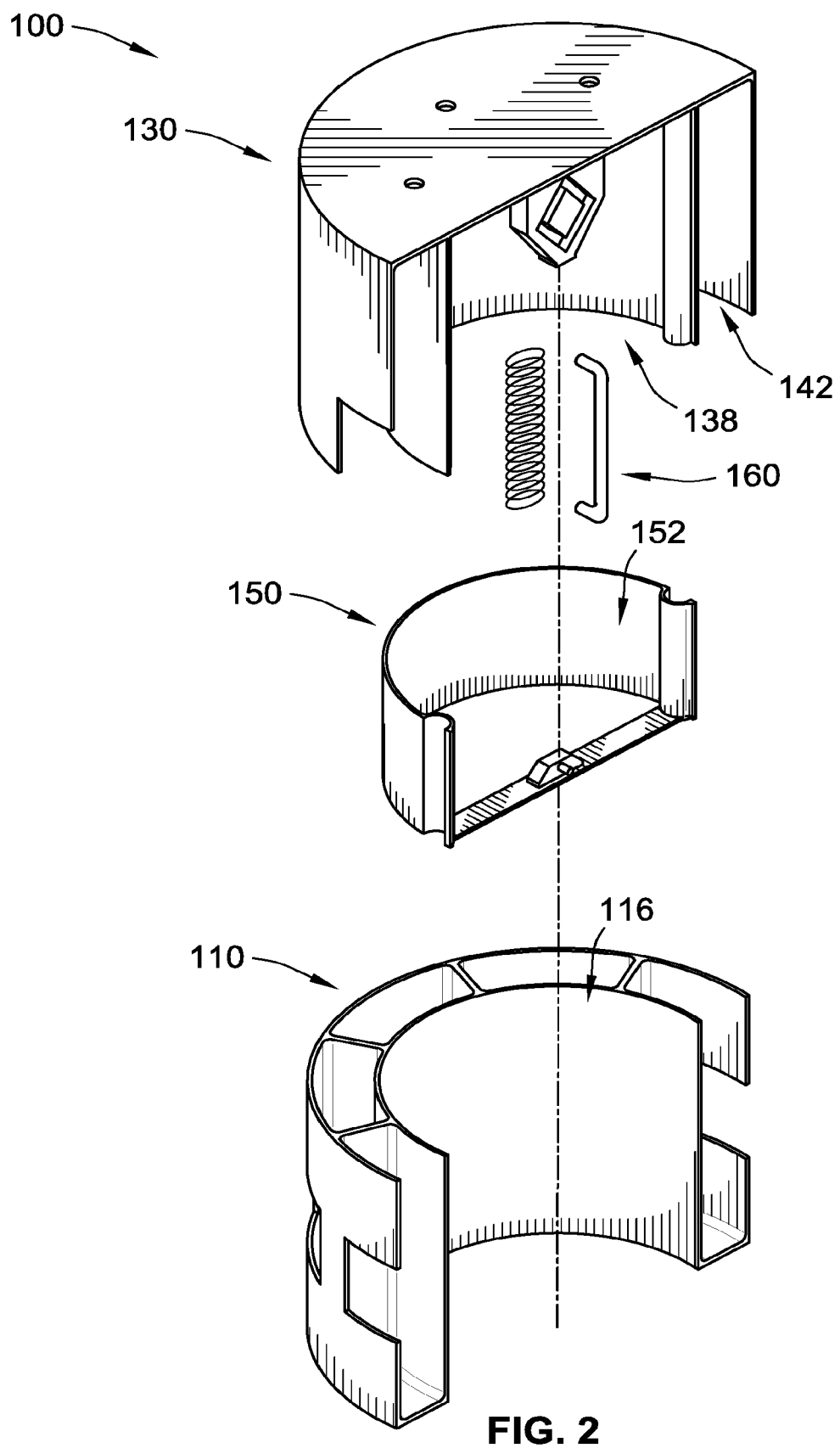
FIG. 2 is an exploded view of the device of FIG. 1 with a portion removed for illustrative purposes.

Generally referring to FIGS. 1 and 2, a device 100 for selectively providing an odor rich environment includes a housing 110, a cover 130, a base 150, and a push-push mechanism 160. In some embodiments, the device 100 is portable and may be hand-held. Generally, the device 100 is used to selectively emit at least one fragrance stored in the housing 110 when the cover 130 is in an open position, thereby providing an odor-rich environment. The odor-rich environment can be used to assist in preventing and/or treating postoperative delirium (POD), cognitive dysfunction (POCD), and/or pain in a subject.

Referring to FIG. 2, the housing 110 includes a base portion 112, an inner sidewall 114, a central cavity 116, an outer sidewall 118, and a plurality of chambers 120. The inner sidewall 114 extends from the base portion 112 and has an inner surface 115a and an outer surface 115b. The central cavity 116 is defined by the inner surface 115a of the inner sidewall 114. The outer sidewall 118 extends from the base portion 112 and has an inner surface 119a and an outer surface 119b. As shown, the inner sidewall 114 and the outer sidewall 118 each have a generally cylindrical configuration and are generally concentric. Further, the outer sidewall 118 has a diameter that is substantially equal to a diameter of the base portion 112 and greater than a diameter of the inner sidewall 114.

Each of the plurality of chambers 120 is formed by the outer surface 115b of the inner sidewall 114, the inner surface 119a of the outer sidewall 118, and a plurality of partitions 124. Each of the plurality of chambers 120 is generally sized and shaped to store a fragrance (not shown) therein. As shown, each of the plurality of chambers 120 is radially distributed around the periphery of the central cavity 116. In the illustrated embodiment, the plurality of partitions 124 are generally evenly spaced relative to one another such that each of the plurality of chambers 120 has substantially the same volume. Alternatively, the plurality of partitions 124 can be spaced relative to one another such that one or more of the plurality of chambers 120 has a different volume than a different one of the plurality of chambers 120. While the plurality of chambers 120 is depicted as being nine chambers, any number of chambers is possible, such as, for example, two chambers, three chambers, six chambers, twelve chambers, fifteen chambers, twenty chambers, forty chambers, etc.

Each of the plurality of chambers 120 includes a respective outlet formed on the outer sidewall 118. The respective outlet 128 of each of the plurality of chambers 120 facilitates fluid communication between each of the plurality of chambers 120 and an exterior of the housing 110. As shown, the respective outlet 128 of each of the plurality of chambers 120 has a generally rectangular configuration; however, alternative configurations are possible, such as, but not limited to, a circular configuration, a triangular configuration, a polygonal configuration, any combination thereof, or the like. The size of the respective outlet 128 of each of the plurality of chambers 120 is proportional to the amount of air that is exchanged between the plurality of chambers 120 and an exterior of the housing 110 via the outlet 128. In some embodiments, the size of the respective outlets 128 is selected based on how much fragrance is desired to be emitted from the device 100, the concentration of the fragrance, combinations thereof, or the like.

The base portion 112, the inner sidewall 114, the outer sidewall 118, and the plurality of partitions 124 of the housing 110 can be made from a metal material, a polymer material, an organic material (e.g., wood), any other suitable material, or any combination thereof. Further, as shown, the base portion 112, the inner sidewall 114, the outer sidewall 118, and the plurality of partitions 124 are unitary and/or monolithic elements. However, other mechanisms for attaching the base portion 112, the inner sidewall 114, the outer sidewall 118, and the plurality of partitions 124 are contemplated, such as, for example, a welded connection, an adhesive or glue connection, a pin and aperture system, tabs, or the like.

Further, while the base portion 112, the inner sidewall 114, and the outer sidewall 118 are depicted as having generally cylindrical configurations, any other configurations are possible, such as, for example, a rectangular configuration, a triangular configuration, a polygonal configuration, any combinations thereof, or the like. In some embodiments, the outer sidewall 118 of the housing and the base portion 112 has a diameter that is between about two inches and about twenty inches. For example, in some implementations, the base portion 112 and the outer sidewall 118 have a diameter that is about six and one-half inches. In some embodiments, the inner sidewall 114 and the outer sidewall 118 have a height that is between about one inch and about ten inches. For example, in some implementations, the inner sidewall 114 and the outer sidewall 118 have a height that is about three and one-half inches.

Figure 3A:
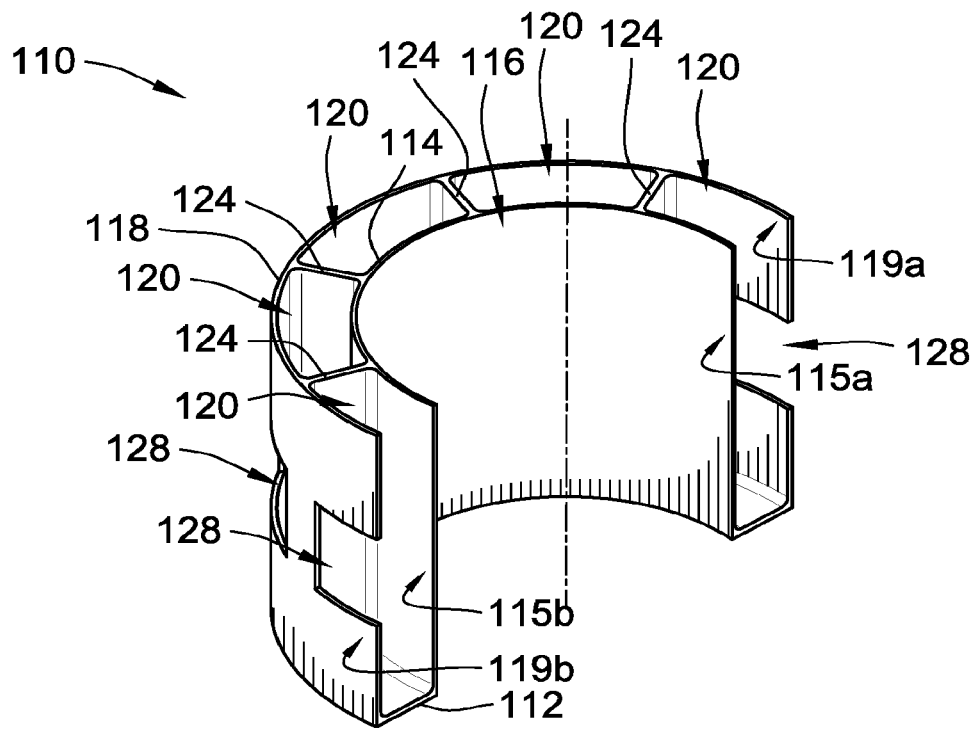
FIG. 3A is a perspective view of a housing of the device of FIG. 1 with a portion removed for illustrative purposes.
Figure 3B:
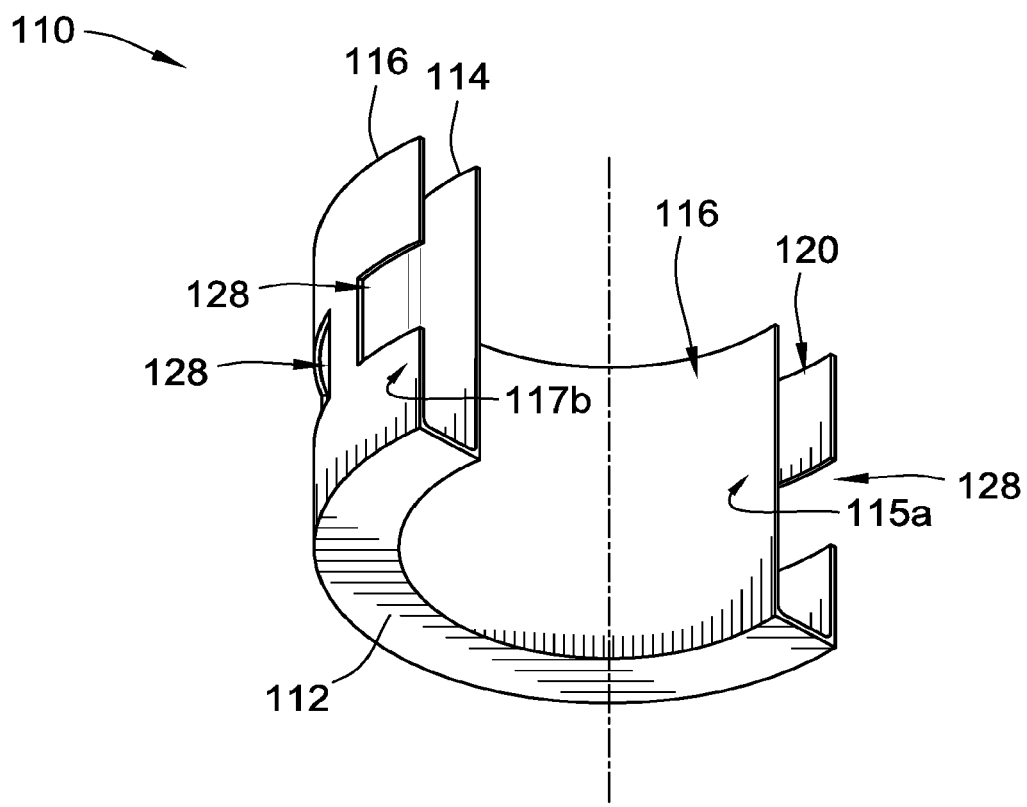
FIG. 3B is another perspective view of the housing of FIGS. 1 and 3A.

Referring to FIGS. 3A and 3B, the cover 130 includes a top portion 132, an interior sidewall 134, an exterior sidewall 136, and a plurality of vents 144. The top portion 132 includes an exterior surface 133a and an interior surface 133b. The interior sidewall 134 extends from the interior surface 133b of the top portion 132 and has an inner surface 135a and an outer surface 135b. Similarly, the exterior sidewall 136 extends from the interior surface 133b of the top portion 132 and has an inner surface 137a and an outer surface 137b. As shown, the interior sidewall 134 and the exterior sidewall 136 both have a generally cylindrical configuration and are generally concentric, and the exterior sidewall 136 has a diameter that is substantially equal to a diameter of the top portion 132 and greater than a diameter of the interior sidewall 134.

The inner surface 135a of the interior sidewall 134 defines an inner chamber 138 of the cover 130. Similarly, the outer surface 135b of the interior sidewall 134 and the inner surface 137a of the exterior sidewall 136 form an outer chamber 142 that is sized and shaped to receive a portion of the housing 110 therein. As shown, the inner surface 135a of the interior sidewall 134 includes a pair of protrusions 140 extending into the inner chamber 138. The pair of protrusions 140 have a general "U"-shape configuration, although any other configuration is possible (e.g., a generally "V"-shape configuration, a generally polygonal shape configuration, or the like). Further, while illustrated embodiment is depicted as having two protrusions, any number of protrusions is possible, such as, for example, one protrusion, four protrusions, six protrusions, etc.

As shown, the plurality of vents 144 is formed on the exterior sidewall 136 of the cover 130. Each of the plurality of vents 144 facilitates fluid communication between the outer chamber 142 and an exterior of the cover 130. Each of the plurality of vents 144 has a generally rectangular configuration and is generally evenly spaced relative to the other of the plurality of vents 144 along the outer surface 137a of the exterior sidewall 136 of the cover 130. Further, in the illustrated embodiment, each of the plurality of vents 144 is substantially the same size and shape as the outlet 128 of each of the plurality of chambers 120 of the housing 110. In other embodiments, each of the plurality of vents 144 can have a shape, configuration, and/or size that is different from another one of the plurality of vents 144, or a shape, configuration, and/or size that is different from the shape, configuration, and/or size of the respective outlet 128 of each of the plurality of chambers 120 of the housing 110.

While the plurality of vents 144 is shown has having three vents, any number of vents is possible, such as, for example, one vent, six vents, ten vents, twenty vents, etc. Further, while the plurality of vents 144 is shown as being evenly spaced along the outer surface 137a of the exterior sidewall 136, the plurality of vents 144 can be positioned relative to one another such that a distance along the outer surface 137a of the exterior sidewall 136 between a first one of the plurality of vents 144 and a second one of the plurality of vents 144 is greater than a distance between the second one of the plurality of vents 144 and a third one of the plurality of vents 144.

The top portion 132, the interior sidewall 134, and the exterior sidewall 136 can be made from a metal material, a polymer material, an organic material (e.g., wood), any other suitable material, or any combination thereof. Further, in the illustrated embodiment, the top portion 132, the interior sidewall 134, and the exterior sidewall 136 are unitary and/or monolithic elements. However, other mechanisms for attaching the top portion 132, the interior sidewall 134, and the exterior sidewall 136 are possible, such as, for example, a welded connection, an adhesive or glue connection, a pin and aperture system, tabs, or the like.

While the top portion 132, the interior sidewall 134, and the exterior sidewall 136 are depicted as having generally cylindrical configurations, any other configurations are possible, such as, for example, a rectangular configuration, a triangular configuration, a polygonal configuration, any combination thereof, or the like. In some embodiments, the exterior sidewall 136 and the top portion 132 have a diameter that is between about two inches and about twenty inches. For example, in some implementations, the top portion 132 and the exterior sidewall 136 have a diameter that is about six and one-half inches. In some embodiments, the interior sidewall 134 and the exterior sidewall 136 have a height that is between about one inch and about ten inches. For example, in some implementations, the interior sidewall 134 and the exterior sidewall 136 have a height that is about three and one-half inches.

The top portion 132 of the cover 130 can also optionally include a plurality of apertures 146 extending between the interior surface 133b and the exterior surface 133a of the top portion 132. In such implementations, the plurality of apertures 146 are sized and shaped such that a light (not shown)

disposed or partially disposed within the inner chamber 138 of the cover 130 is visible from the exterior surface 133a of the top portion 132. The light can be, for example, a light emitting diode ("LED"). Each light can be powered by a power supply (not shown) and controlled by a processor and/or memory (not shown) that is disposed within the inner chamber 138 of the cover 130. Alternatively, each light can be powered by an external power source. The lights can be used to provide visual stimulation to a subject, indicate a rotated position of the cover 130 relative to the housing 110, or the like.

Figure 6A:
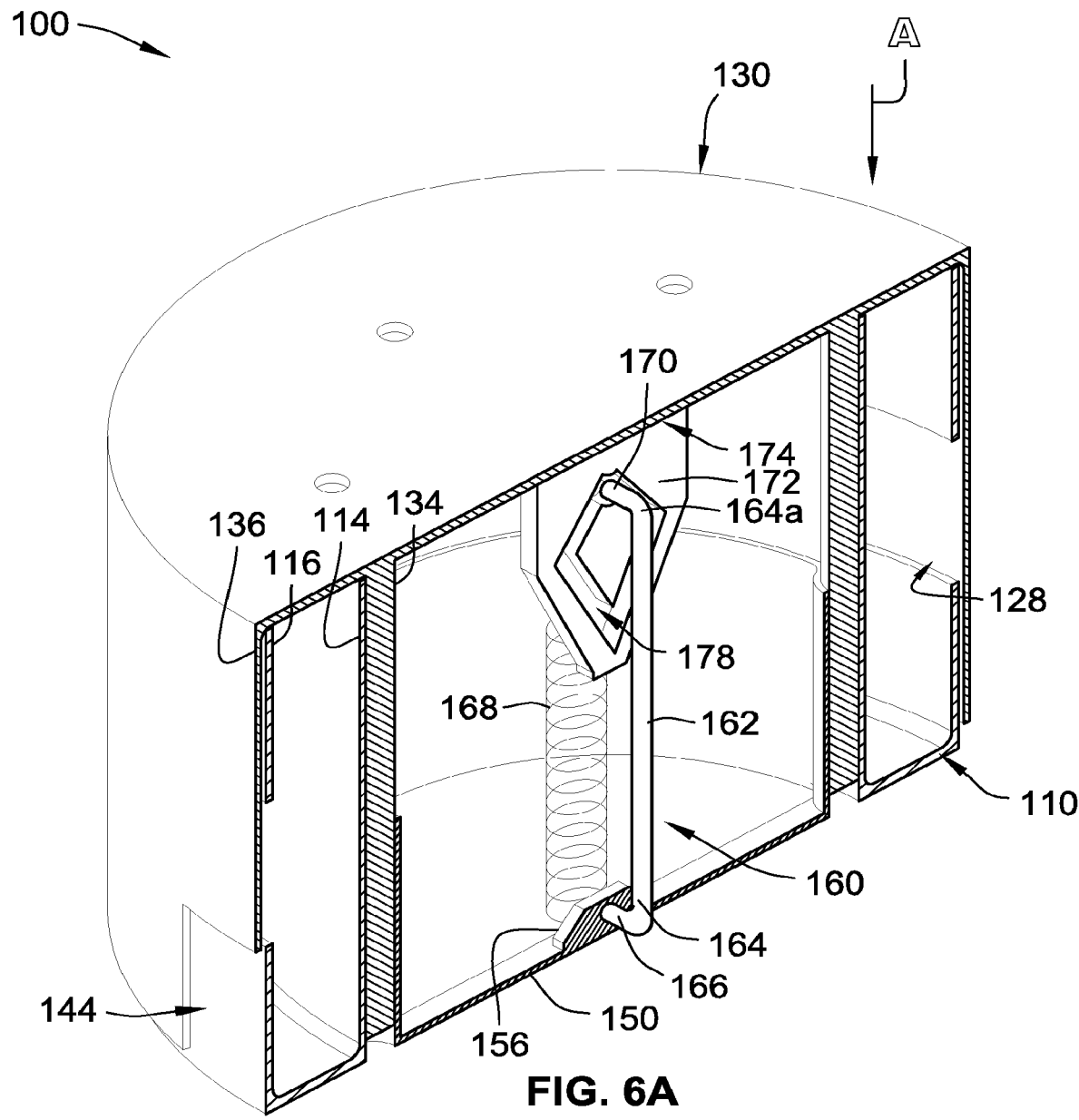
FIG. 6A is a cross-sectional perspective view of the device of FIG. 1 showing a push-push mechanism.
Figure 6B:
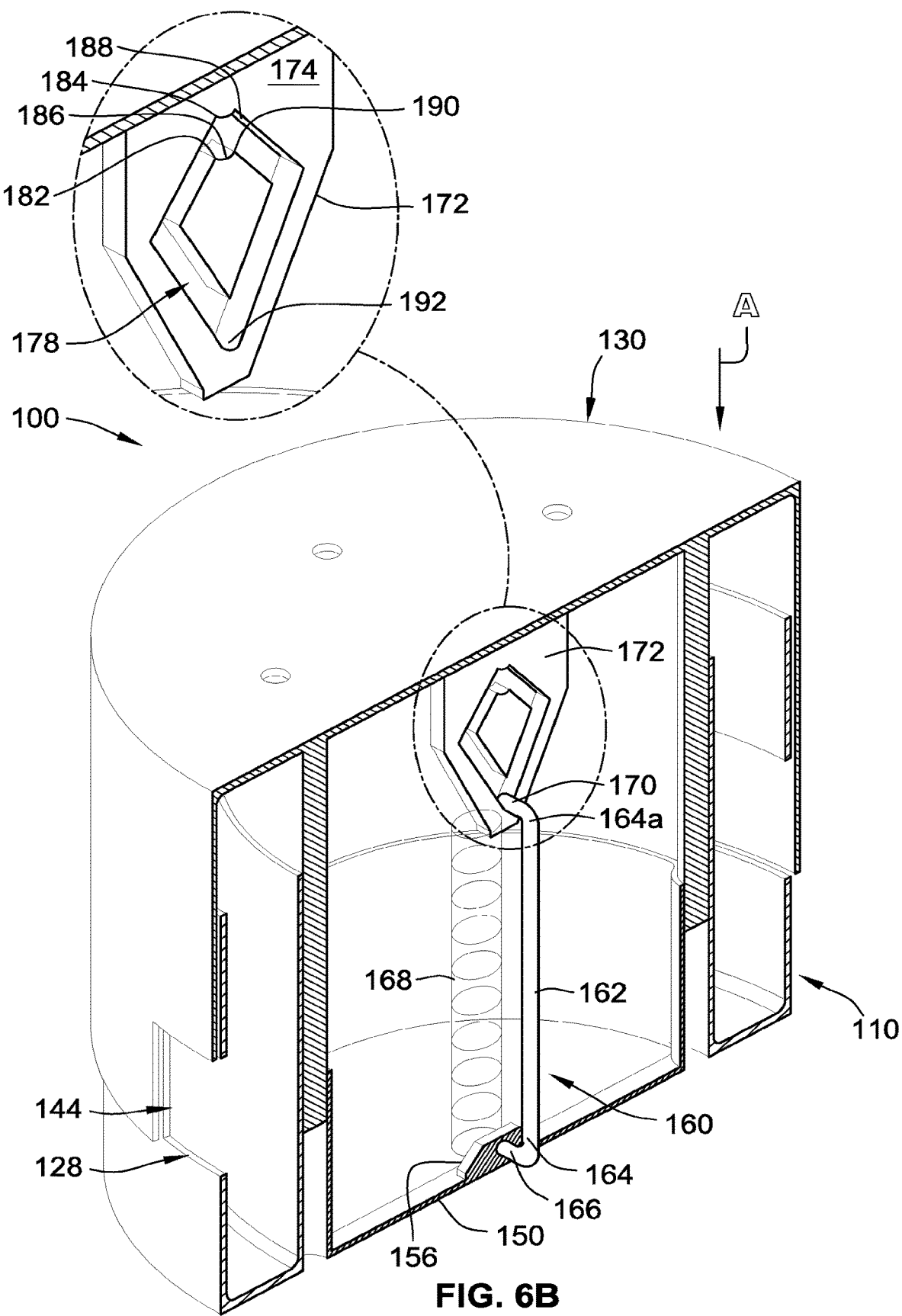
FIG. 6B is another cross-sectional perspective view of the push-push mechanism of FIG. 6A.

As best shown in FIGS. 6A and 6B, the outer chamber 142 of the cover 130 is sized and shaped to receive a portion of the housing 110 therein. Specifically, the inner surface 137a of the exterior sidewall 136 of the cover 130 slidably engages the outer surface 119a of the outer sidewall 118 of the housing 110, and the outer surface 135b of the interior sidewall 134 of the cover slidably engages the inner surface 115a of the inner sidewall 114 of the housing 110. Thus, the cover 130 can move up and down relative to the housing 110 and/or rotate relative to the housing 110.

Figure 4A:
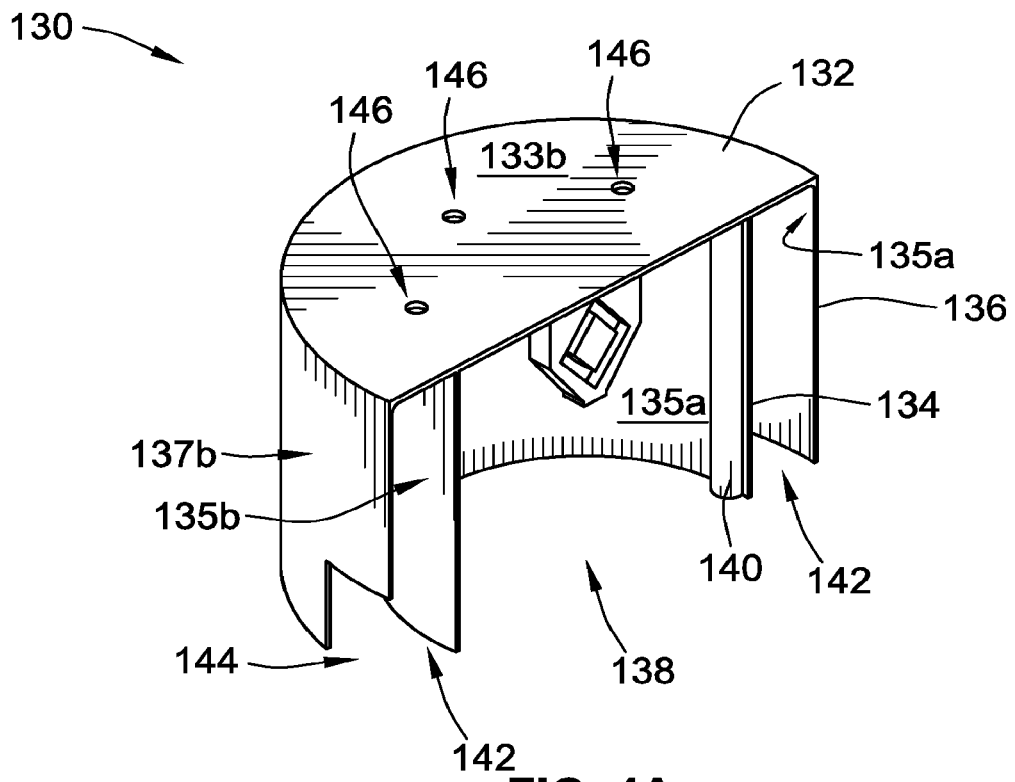
FIG. 4A is a perspective view of a cover of the device of FIG. 1 with a portion removed for illustrative purposes.
Figure 4B:
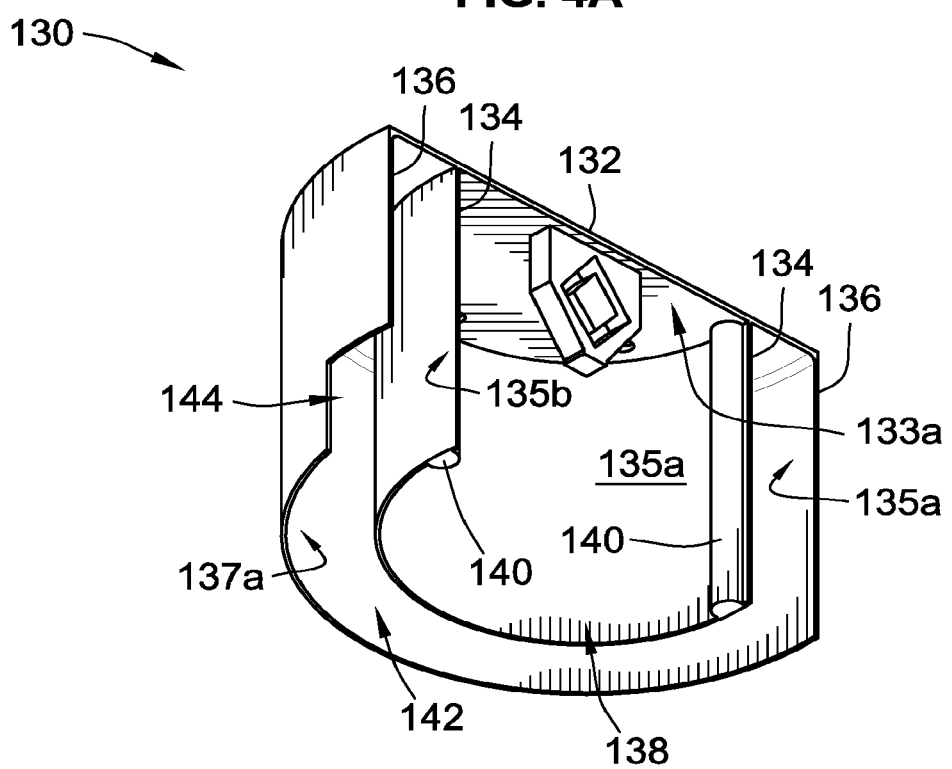
FIG. 4B is another perspective view of the cover of FIGS. 1 and 4A.
Figure 5A:
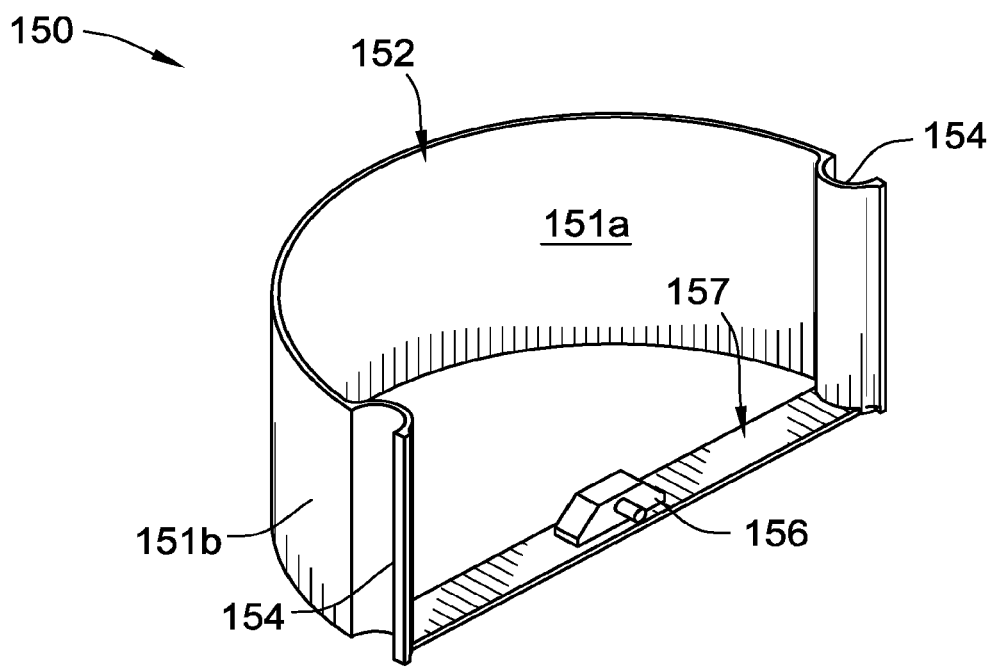
FIG. 5A is a perspective view of a base of the device of FIG. 1 with a portion removed for illustrative purposes.
Figure 5B:
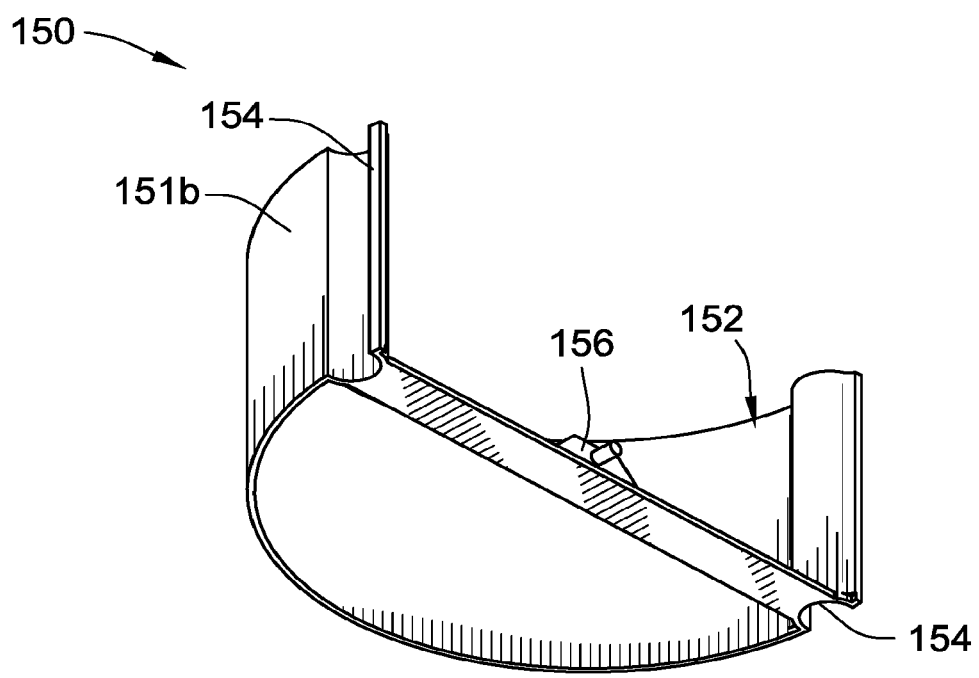
FIG. 5B is another perspective view of the base of FIGS. 1 and 5A.

Referring to FIG. 4, the base 150 includes a central cavity 152, a pair of recesses 154, and a push-rod support 156. The base 150 has a generally cylindrical configuration, an inner generally vertical surface 151a, and an outer generally vertical surface 151b. The pair of recesses 154 extends into the central cavity 152 and have a generally "U"-shaped configuration that is adapted to mate with (i.e., be generally flush with) the pair of protrusions 140 of the cover 130. The push-rod support 156 extends from or is coupled with a bottom inner surface 157 of the base 150. The base 150 has a generally cylindrical configuration and can be made of a metal material, a polymer material, an organic material (e.g., wood), any other suitable material, or any combination thereof.

Referring to FIGS. 6A and 6B, the push-push mechanism 160 includes a push rod 162, a biasing spring 168, a cam follower 170, and a cam 172. The push rod 162 has a first end 164a and a second end 164b. The first end 164a of the push rod 162 is coupled to a pivot point 166 that is formed on or coupled with the push-rod support 156 of the base 150. The pivot point 166 is configured to permit the push rod 162 to rotate about the pivot point 166. The second end 164b of the push rod 162 is coupled to the cam follower 170, which extends from the push rod 162 and has a generally cylindrical configuration. The push rod 162 can be made of a metal material, a polymer material, any other suitable material, or any combination thereof.

The cam 172 includes an open face 174, a bottom surface 176, and a cam path 178. The cam 172 is extends from and/or is coupled with the interior surface 133b of the top portion 132 of the cover 130 and extends into the inner chamber 138 of the cover 130. As shown, the cam 172 and the top portion 132 of the cover 130 are unitary and/or monolithic. However, various mechanisms for coupling the cam 172 to the top portion 132 of the cover 130 are possible, such as, for example, an adhesive connection, a welded connection, a threaded connection, a pin and aperture system, any other suitable connection, or any combination thereof.

The cam path 178 is formed on the open face 174 of the cam 172 and has a generally diamond-shaped configuration, although other configurations are possible, such as, for example, a generally oval configuration, a generally circular configuration, or the like. As best shown in FIG. 6C the cam path 178 includes a first corner 182, a second corner 184, a top recess 186, a third corner 188, a fourth corner 190, and a bottom recess 192. The cam follower 170 is sized and shaped to slidably engage the cam path 178.

As shown, the biasing spring 168 is positioned between the push-rod support 156 of the base 150 and the bottom surface 176 of the cam 172. The biasing spring 168 urges the cam 172 and, thus, the cover 130 away from the base 150 (i.e., in the opposite direction of arrow A) and resists movement of the cover 130 towards the base 150. The spring constant of the biasing spring 168 can be varied to provide a desired level of resistance.

While the cam 172 of the push-push mechanism 160 is described above as being formed on or coupled with the cover 130, and the pivot point 166 is described as being formed on or coupled with the base 150, in some implementations, the device 100 includes a push-push mechanism wherein the cam 172 is coupled to the base 150 and the pivot point 166 is formed on the cover 130. In such implementations, the push-push mechanism operates in the same or similar manner as the push-push mechanism 160.

As best shown in FIGS. 6A and 6B, the base 150 is disposed within the inner chamber 138 of the cover 130. The pair of protrusions 140 of the interior sidewall 134 of the cover 130 slidably engage the pair of recesses 154 of the base 150, thereby substantially preventing rotation of the base 150 relative to the cover 130, and vice versa. The slidable engagement of the pair of protrusions 140 and the pair of recesses 154 permits the cover 130 to move up and down relative to the base 150, which remains generally stationary. As described above, the push-push mechanism 160 is disposed within the central cavity 152 of the base and the inner chamber 138 of the cover 130.

In some implementations, the base 150 can include a pair of protrusions (not shown) and the cover 130 can include a pair of recesses (not shown). In the configuration, the pair of protrusions of the base 150 engages the pair of recesses of the cover 130 in the same or similar manner as the pair of protrusions 140 and pair of recesses 154 described above. Alternatively, any other suitable mechanism can be used to relative rotation of the base 150 relative to the cover 130, and vice versa, while permitting the cover 130 to move up and move relative to the base.

Figure 7A:
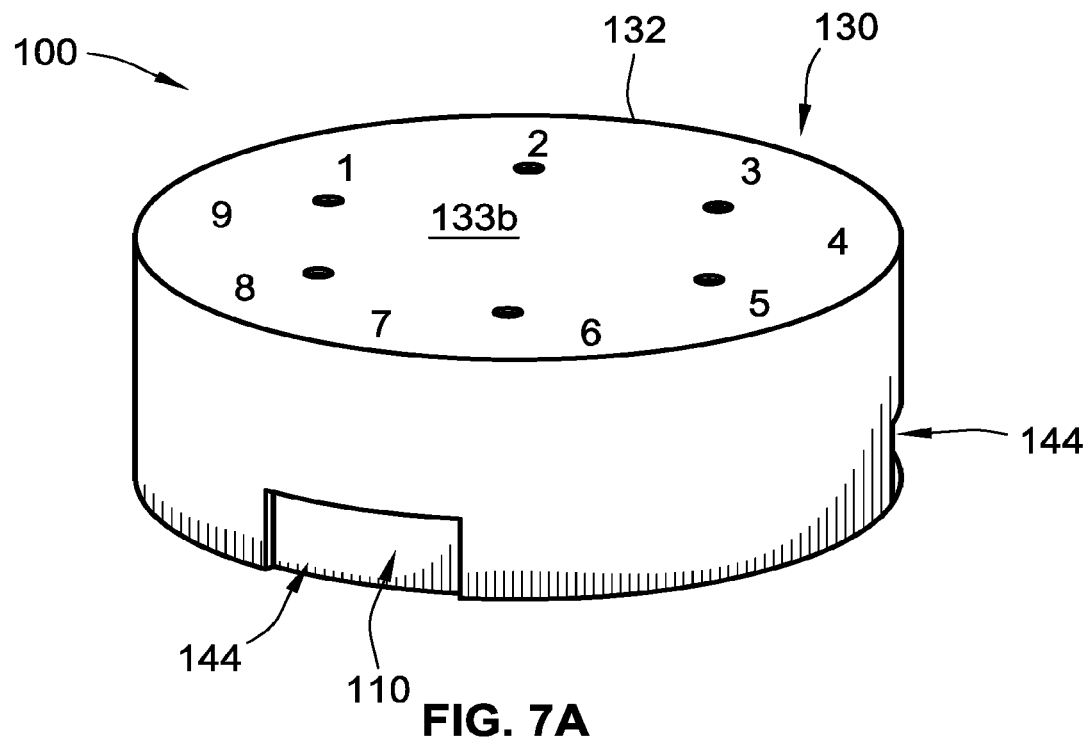
FIG. 7A is a perspective view of the device of FIG. 1 with the cover in a closed position.
Figure 7B:
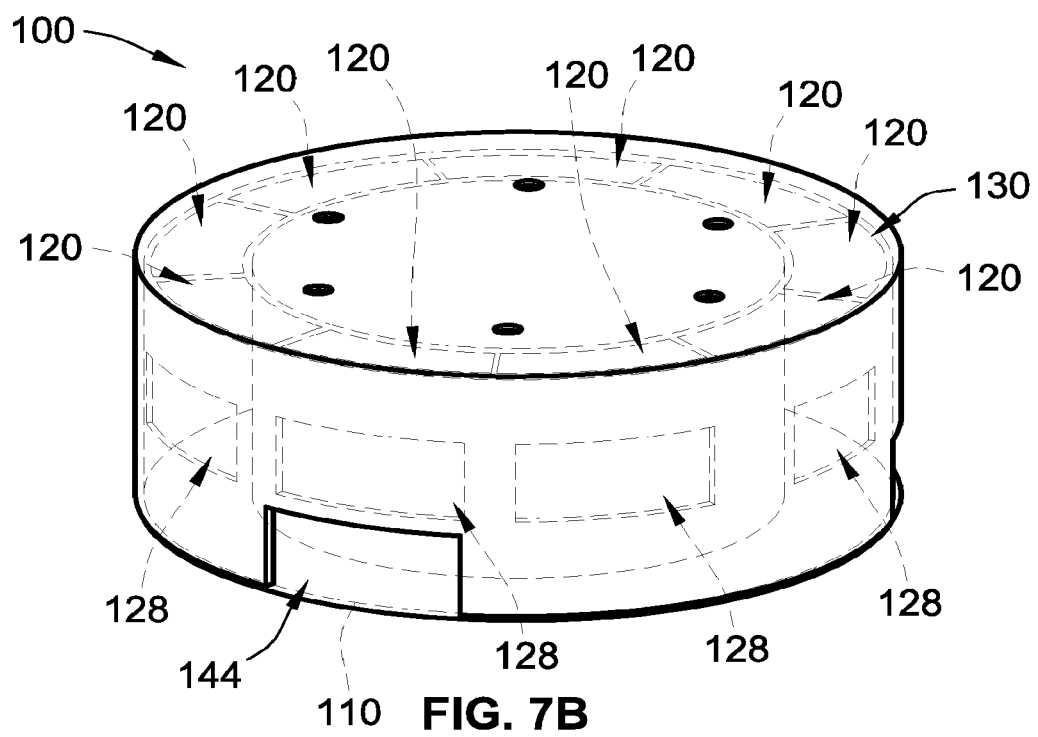
FIG. 7B is a partial cross-sectional view of the device of FIGS. 1 and 7A.

Generally referring to FIGS. 7A and 7B, the cover 130 is shown in a closed position. In the closed position, the inner surface 137a of the exterior sidewall 136 of the cover 130 substantially overlaps the outlet 128 of each of the plurality of chambers 120 (FIG. 7B), thereby inhibiting or preventing fluid communication between the plurality of chambers 120 and an exterior of the device 100.

As best shown in FIG. 6A, when the cover 130 is in the closed position, the cam follower 170 of the push-push mechanism 160 engages the top recess 186 of the cam path 178 (FIG. 6C). The biasing spring 168 urges the cam 172, and thus the top recess 186, away from the base 150. As a result, the biasing spring 168 causes the top recess 186 to apply a force to the cam follower in the opposite direction of arrow A, which, in turn, applies the same force to the push rod 162. Because the push rod 162 is coupled to the base 150, which remains stationary relative to the cover 130, the push rod 162 inhibits or prevents further movement of the cam 172 away from the base 150. Thus, the interaction between the biasing spring 168 and the cam 172 and the interaction between the push rod 162 and the base 150, aid in generally maintaining the cover 130 in the closed position.

Figure 8A:
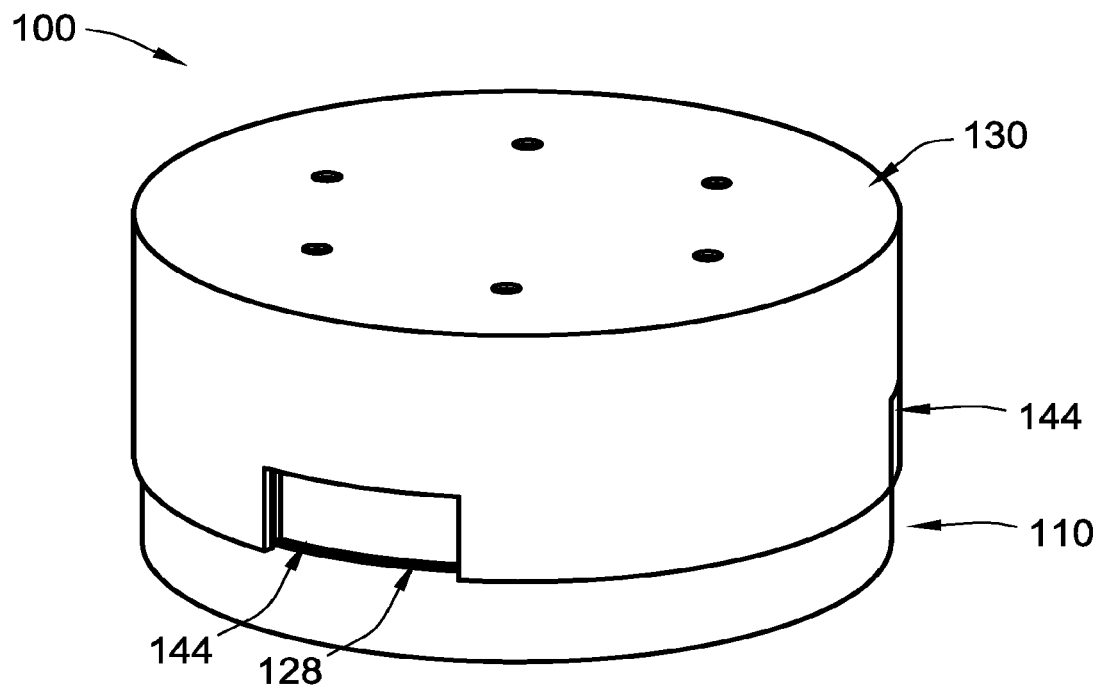
FIG. 8A is a perspective view of the device of FIG. 1 with the cover in the open position.
Figure 8B:
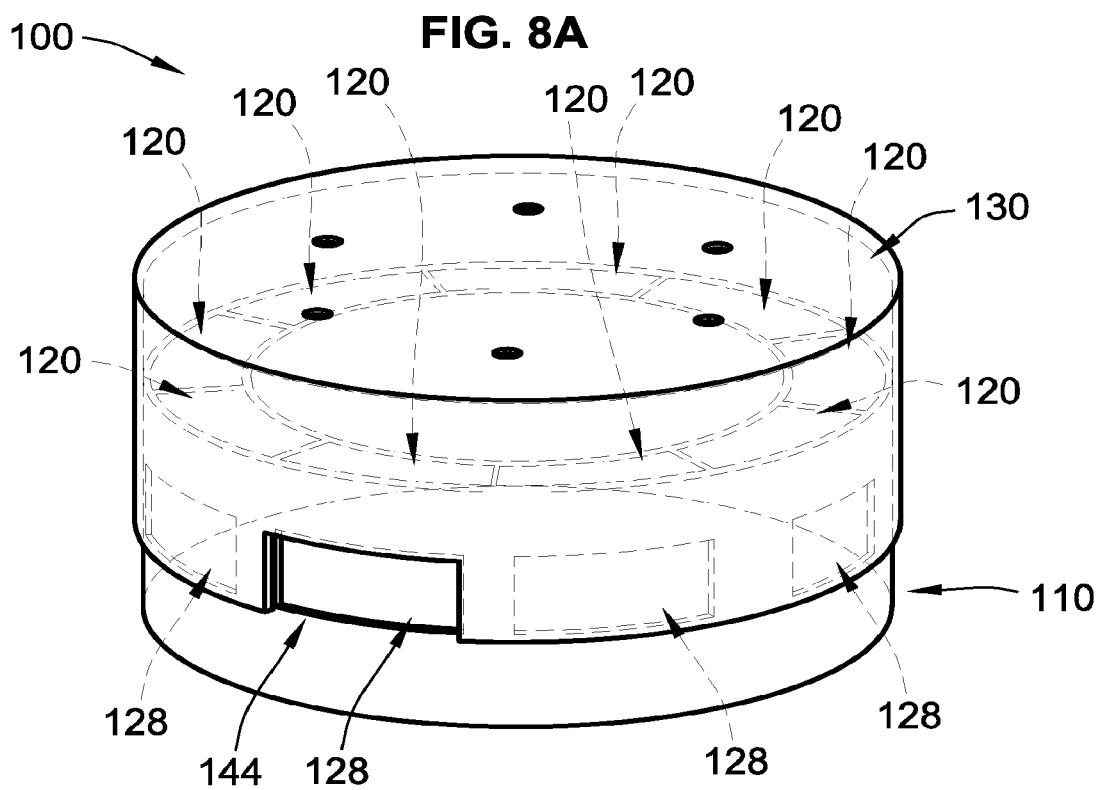
FIG. 8B is a partial cross-sectional view of the device of FIGS. 1 and 8A.

Generally referring to FIGS. 8A and 8B, the cover 130 is shown in an open position. In the open position, each of the plurality of vents 144 of the cover 130 at least partially overlaps at least one outlet 128 of the plurality of chambers 120 of the housing 110. Thus, when the cover 130 is in the open position, at least one of the plurality of vents 144 is generally adjacent to the respective outlet 128 of at least one of the plurality of chambers 120. In this configuration, the respective outlet 128 and the at least one of the plurality of vents 144 at least partially overlap such that the respective one of the plurality of chambers 120 is in fluid with an exterior of the device (e.g., the atmosphere), thereby permitting air to be exchanged between the at least one of the plurality of chambers 120 and the exterior of the device 100.

Figure 9:
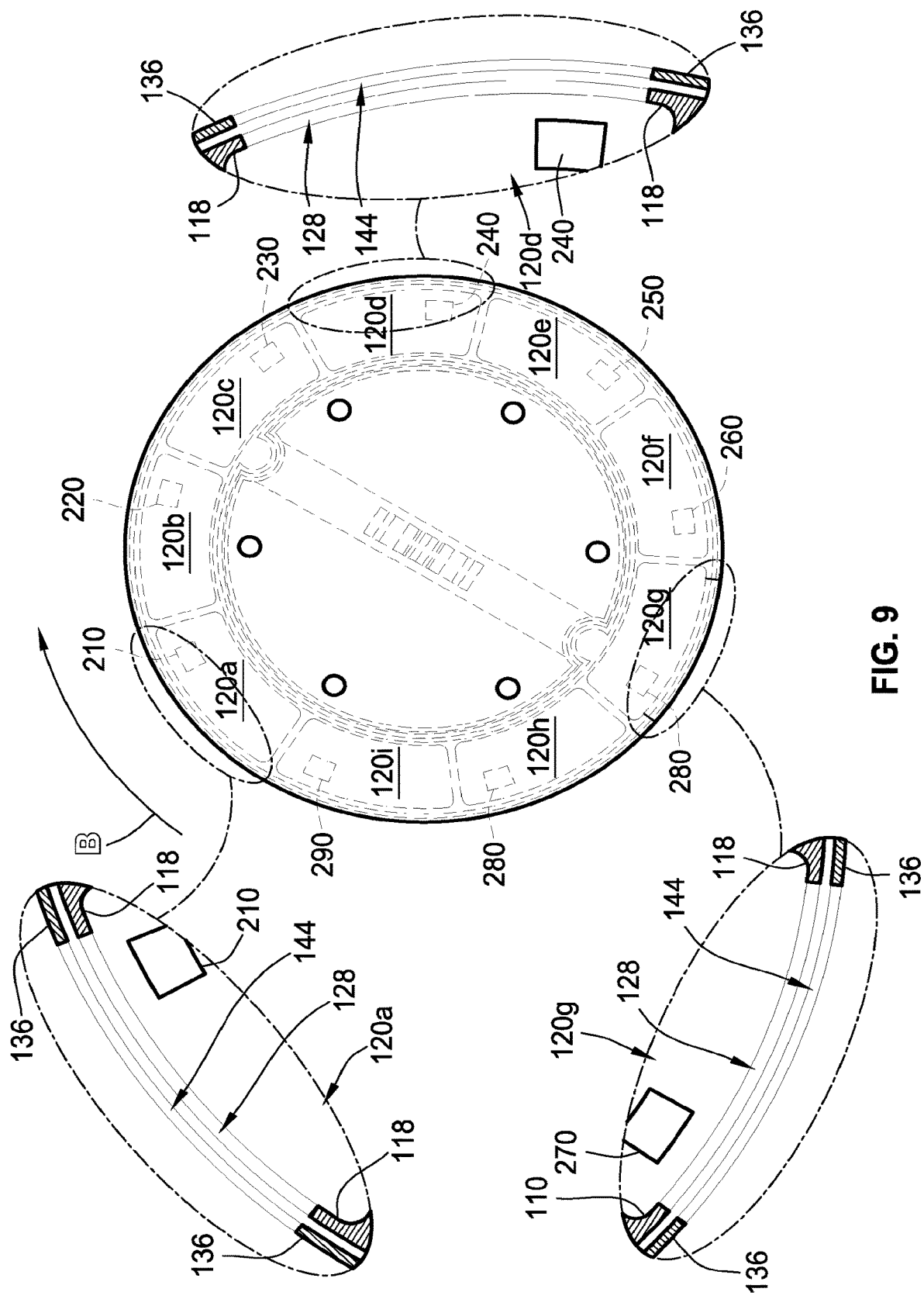
FIG. 9 is a top cross-sectional view of the device of FIG. 1.

When the cover 130 is in the open position, the cover 130 can be rotated relative to the housing 110. Referring to FIG. 9, the cover 130 is shown in a first rotated position wherein each of the plurality of vents 144 substantially overlaps an outlet 128 of a respective one of the plurality of chambers 120 of the housing 110. As the cover 130 rotates towards a second rotated position in the direction of arrow B, each of the plurality of vents 144 rotates relative to the outlet 128 it substantially overlapped in the first rotated position. When the cover 130 is rotated in the direction of arrow B and away from the first rotated position shown in FIG. 9, each of the plurality of vents 144 rotates relative to the housing 110 and partially overlaps the respective outlets 128 of two of the plurality of chambers 120. In this position, six of the plurality of chambers 120 are in fluid communication with the exterior of the device 100. As the cover 130 continues to rotate relative to the housing 110, each of the plurality of vents 144 substantially overlaps the respective outlet 128 of one of the plurality of chambers 120 directly adjacent to the respective outlet 128 that it substantially overlapped in the prior rotated position. In this manner, a user can rotate the cover 130 such that the plurality of vents 144 substantially completely overlaps the respective outlet 128 of three of the plurality of chambers 120, or partially overlaps the respective outlet 128 of six of the plurality of chambers 120.

As best shown in FIG. 6B, when the cover 130 is in the open position, the cam follower 170 of the push-push mechanism 160 engages the bottom recess 192 of the cam path 178. The biasing spring 168 urges the cam 172 and, thus, the bottom recess 192 of the cam path 178, away from the base 150. As a result, the biasing spring 168 causes the bottom recess 192 to apply a force on the cam follower 170 in the direction of arrow A which, in turn, applies the same force to the push rod 162. Because the push rod 162 is formed on or coupled with the base 150, which remains generally stationary relative to the cover 130, the push rod 162 and the cam follower 170 substantially prevent further movement of the cam 172 away from the base 150. Thus, the interaction between the biasing spring 168 and the cam 172 and the interaction between the push rod 162 and the base 150 aid in maintaining the cover 130 in the open position.

To transition the cover 130 from the closed position to the open position, a user may apply a force on the cover 130 in the direction of arrow A, or the base 150 in the opposite direction of arrow A. The force compresses the biasing spring 168 of the push-push mechanism 160 and moves the cover 130 and, thus, the cam 172, towards the base 150. With the biasing spring 168 in a compressed position, the bottom recess 192 moves away from the base 150 and disengages the cam follower 170. The cam follower 170 then engages the third corner 188 of the cam path 178. When the force is removed from the cover 130, the biasing spring 168 urges the cam 172 away from the base 150. Due to this movement of the cam 172, the cam follower 170 moves adjacent to the fourth corner 190, and the biasing spring 168 urges the cam 172 in the opposite direction of arrow A such that the cam follower 170 moves along the cam path 178 towards the bottom recess 192. As the cam follower 170 moves along the cam path 178, the push rod 162 pivots about the pivot point 166 on the base 150. The cam follower 170 then engages the bottom recess 192, causing the cover 130 to be in the open position, as shown in FIG. 6B.

The push-push mechanism 160 transitions the cover 130 from the open position to the closed position in a similar manner. With the cover 130 in the open position, the same force described above for transitioning the cover 130 from the closed position to the open position is applied. The force compresses the biasing spring 168, which causes the cam 172 and, thus, the bottom recess 192, to move away from the base 150, causing the bottom recess 192 to disengage the cam follower 170. The cam follower 170 then engages the first corner 182 of the cam path 178. When the force is removed from the cover 130 or the base 150, the biasing spring 168 urges the cam 172 away from the base 150, causing the cam follower 170 to move past the second corner 184 and move along the cam path 178. The cam follower 170 then engages the top recess 186 as described above, causing the cover 130 to be in the closed position.

While the cover 130 is described above as being transitioned between the open position and the closed position via the push-push mechanism 160, other mechanisms for transitioning and/or maintaining the cover 130 in the open and closed positions are possible. For example, the device 100 can include a touch/push latch, a cam and plunger mechanism (e.g., similar to a click pin), any combination thereof, or the like that transitions the cover between the open and closed positions. Further, in some implementations, rather than slidably engaging the housing 110 and the cover 130, the housing 110 and cover 130 can be coupled by a threaded connection. In such implementations, the respective outlets 128 of the plurality of chambers 120 and/or of the plurality of vents 144 can be arranged in an ascending stair-case like arrangement. As the cover 130 and/or housing 110 is rotated, the cover 130 moves up or down relative to the housing 110 via the threaded connection therebetween. In this manner, the cover 130 can be moved between an open position and a closed position, and fragrances stored in the plurality of chambers 120 can be emitted in a similar fashion as described above.

As described above, each of the plurality of chambers 120 of the housing is sized and shaped to store a predefined fragrance therein. The predefined fragrance can be scented oil, scented paper, one or more scented beads, incense, potpourri, other active aerosol ingredients, other aromatic ingredients, any combination thereof, or the like. For example, the predefined fragrance stored in each of the plurality of chambers 120 of the housing 110 can be one or more of the following fragrances: rose, peppermint, vanilla, ketchup, yeast extract, coffee, onion, dried fungus, soy sauce, strawberry, ginger, pu-erh tea, cumin, honey, olive oil, chocolate, shrimp, sausage, cucumber, apple, tomato, banana, celery, walnut, garlic, cinnamon, date, white pepper, sweet potato, peppercorn oil, caraway, vinegar, kiwi, shallot, brown sugar, grape, pear, curry, eggplant, fig, carrot, leak, or any combination thereof, or the like.

As shown in the illustrated embodiment, the plurality of chambers 120 of the housing is nine chambers, and the plurality of vents 144 of the cover 130 is three vents. Referring FIG. 9, by way of example, a first fragrance 210 is disposed in a first chamber 120$a$, a second fragrance 220 is disposed in a second chamber 120$b$, a third fragrance 230 is disposed in a third chamber 120$c$, a fourth fragrance 240 is disposed in a fourth chamber 120$d$, a fifth fragrance 250 is disposed in a fifth chamber 120e, a sixth fragrance 260 is disposed in a sixth chamber 120f, a seventh fragrance 270 is disposed in a seventh chamber 120g, an eighth fragrance 280 is disposed in an eighth chamber 120h, and a ninth fragrance 290 is disposed in a ninth chamber 120i. Each of the fragrances 210, 220, 230, 240, 250, 260, 270, 280, and 290 can be the same fragrance, a different fragrance, or a combination thereof.

As shown in FIG. 9, the cover 130 is in the open position and in a first rotated position wherein the plurality of vents 144 completely overlaps the respective outlet 128 of the first chamber 120a, the fourth chamber 120d, and the seventh chamber 120g. As described above, in this configuration, the fragrances 210, 240, and 270 are emitted from the respective outlets 128 and the plurality of vents 144 to the exterior of the device 100. Thus, in the first rotated position shown in FIG. 9, a first fragrance combination which is a combination of fragrances 210, 240, and 270, is radially distributed around the device 100, thereby forming an odor rich environment.

As described above, as the cover 130 is rotated in the direction of arrow B relative to the housing 110 towards a second rotated position, the plurality of vents 144 are positioned between two of the plurality of chambers 120. Specifically, in this rotated position, (i) a first one of the plurality of vents 144 partially overlaps the respective outlets of the first chamber 120a and the second chamber 120b, (ii) a second one of the plurality of vents 144 partially overlaps the respective outlets of the fourth chamber 120d and the fifth chamber 120e, and (iii) a third one of the plurality of vents 144 partially overlaps the respective outlets of the seventh chamber 120g and the eighth chamber 120h. In this configuration, the fragrances 210, 220, 240, 250, 270, and 280 are emitted to the exterior of the device 100. Thus, in this rotated position, a second fragrance combination, which is a combination of fragrances 210, 220, 240, 250, 270, and 280, is radially distributed around the device 100.

By continuing to rotate the cover 130 in the direction of arrow D in the manner described above, up to six preselected fragrance combinations can be emitted from the device 100, depending on the rotated position of the cover 130 relative to the housing 110. Specifically, the six preselected fragrance combinations include: (1) the first preselected fragrance combination described above (the combination of fragrances 210, 240, and 270); (2) the second preselected fragrance combination described above (the combination of fragrances 210, 220, 240, 250, 270, and 280); (3) a third preselected fragrance combination which is a combination of fragrances 220, 250, and 280; (4) a fourth preselected fragrance combination which is a combination of fragrances 220, 230, 250, 260, 280, and 290; (5) a fifth preselected fragrance combination which is a combination of fragrances 230, 260, and 290; and (6) a sixth preselected fragrance combination which is a combination of fragrances 230, 240, 260, 270, 290, and 210. As described above, the number of chambers in the plurality of chambers 120 of the housing 110 and the number of vents in the plurality of vents 144 of the cover 130 can be selected to provide a desired number of preselected fragrance combinations.

In some implementations, the cover 130 includes a plurality of markings [[shown in FIG. 7A]] that are visible when the cover 130 is in the open position. Each of the plurality of markings corresponds with each of the plurality of chambers 120 (e.g., a first marking corresponds with the first chamber 120a). Further, in such implementations, each of the plurality of markings indicates the type of fragrance that is stored within the corresponding one of the plurality of chambers 120. The marking can identify the fragrance stored in each of the plurality of chambers 120 such that a user can rotate the cover 130 to, e.g., align the marking with one of the plurality of vents 144 to emit the fragrance. The markings may include words, symbols, icons, photographs, numbers, any combination thereof, or the like.

In some implementations, the device includes a housing (not shown) that is similar to the housing 110 in that it includes a plurality of chambers, with each of the plurality of chambers having a respective outlet. However, in such implementations, the housing includes a top portion (not shown) and a plurality of sliding vents. The top portion is similar to the cover 130 in that it inhibits fluid communication between an exterior of the housing and the plurality of chambers except via each respective outlet. Each of the plurality of sliding vents is configured to substantially overlap each respective outlet of the plurality of chambers and have an open position and a closed position. Each of the plurality of sliding vents is in the open position, the sliding vent does not overlap, or only partially overlaps, the respective outlet of one of the plurality of chambers such that the chamber is in fluid communication with an exterior of the device. In other implementations, the housing can include a plurality of hinged vents configured to substantially overlap the outlet of each of the plurality of chambers. The plurality of hinged vents are configured to move between and open position and a closed position via a hinge, thus aiding in permitting or inhibiting fluid communication between the plurality of chambers and the exterior of the device as described above.

In some implementations, the device 100 further includes a fan (not shown) disposed within the inner chamber 138 of the cover 130 and/or the central cavity 152 of the base to aid in emitting the fragrances stored within the plurality of chambers 120 through the respective outlets 128 and the plurality of vents 144. In such implementations, the fan extends from and/or is coupled with the inner surface 137a of the top portion 132 of the cover 130, or the bottom inner surface 157 of the base 150. The interior sidewall 134 of the cover includes a plurality of outlets (not shown) such that the inner chamber 138 and the outer chamber 142 of the cover 130 are in fluid communication with one another. Further, each of the plurality of chambers 120 have a second outlet formed in the inner sidewall 114 of the housing such that the plurality of chambers 120 are in fluid communication with the inner chamber. Thus, as the cover 130 rotates, each of the plurality of outlets of the interior sidewall 134 at least partially overlaps one of the second outlets of the plurality of chambers 120. Thus, the fan forces air through the plurality of chambers 120 to aid in emitting the fragrances stored therein from the device 100.

In some implementations, the device 100 further includes a display (not shown) for providing visual simulation and/or a speaker (not shown) for providing audio stimulation. Generally, the display can be any device capable of displaying still photos or video, such as an LCD screen commonly used with smartphones. The display can be positioned in any suitable location on the device 100, including, for example, on the exterior surface 133b of the top portion 132 of the cover 130, on the outer surface 137b of the exterior sidewall 136 of the cover 130, a combination thereof, or the like.

In such implementations, the device 100 can further include, for example, a memory, a processor, a power supply, a sound system, a user interface, and/or a communication element. The memory may store movies, music, pictures, photographs, etc. that can be displayed on the video screen and played through the speaker. In some embodiments, the stored data includes photographs and/or slow moving pictures of the patient's home. The communication element may be configured to communicate with an external source, such as a personal computer, a tablet, a smartphone, and/or a remote server, using WiFi. Thus, the communication element can be used to upload movies, music, pictures, photographs, software updates, etc. from the external source to the memory. Patients and their family members will prepare the contents of the device before the surgery. Further still, in some implementations, the device 100 may include a web camera for remote communication.

In some embodiments, patients and their family members may choose their favorite fragrances, movies, music, pictures, or the like and install them into the device. The device may be configured to remotely receive updated music, movies, pictures, or the like from family members. The family members may also send get-well cards, flower pictures, and the like to the device or website. The device may also allow doctors, nurses, and other healthcare professionals to communicate with family members pre-surgery, during surgery, and/or post-surgery. The communication between patient and family members may assist in reducing the anxiety of patients, e.g., when waiting in a pre-operative holding area before the surgery under anesthesia, which may help to reduce POCD, POD, and/or pain.

In some implementations, the display (not shown) of the device 100 is a touchscreen and the memory includes a game, program, or application for intellectual stimulation. For example, the memory may include a calculation game that displays numbers ranging from between 1 and 14 on the touchscreen (e.g., 6, 3, 14, 6). A user then is prompted to apply a series of mathematical operations to these numbers, with the requirement that the last mathematical calculation in the series yields a solution of 24. For example, if the numbers 6, 3, 14, and 16 are displayed, the user (i) completes a first calculation wherein 3 is subtracted from 6 yielding a solution of 3, (ii) completes a second calculation wherein 6 is subtracted from 14 yielding a solution of 8, and then (iii) completes a third calculation multiplying the solution of the first calculation (3) and the second calculation (8) to arrive at the desired solution of 24. The device records the time that it takes the user to complete the calculation game. It is contemplated that other types of games, programs, or applications for intellectual stimulation may alternatively or additionally be included on the device 100.

In some embodiments, the game includes prompting the patient to identify the fragrance or fragrance combination emitted from the device. A correct answer may be indicated by an icon or message on the display, a sound, a combination thereof, or the like.

In some implementations, the odor-rich environment selectively provided by the device 100 can be used to assist in preventing and/or treating postoperative delirium ("POD"), postoperative cognitive dysfunction ("POCD"), and/or pain. To aid in preventing POD, POCD, and/or postoperative pain, the odor-rich environment is administered to a subject prior to the subject being administered anesthesia. For example, the odor-rich environment can be administered for a period of about 14 days prior to and/or about 14 days after the subject has been administered anesthesia. The odor-rich environment includes at least one preselected fragrance.

In some implementations, the odor-rich environment comprises a fragrance combination that includes a first preselected fragrance and a second preselected fragrance. Subsequent to administering the odor-rich environment to the subject for a first predetermined time period, the fragrance combination can be removed and a second fragrance combination including a third preselected fragrance and a fourth preselected fragrance is provided for a second predetermined time period. The first predetermined time period and the second predetermined time period can be any suitable amount of time, for example, one hour, twelve hours, one day, two days, one week, etc. The predetermined time period(s) for administering the odor-rich environment may be selected based on a variety of factors including, but not limited to, the type of anesthesia given, the patient's predisposition to pain, anxiety, stress, or the like, the type/severity of the surgery, any combination thereof, or the like. In one implementation, the odor-rich environment comprises a different fragrance or fragrance combination each day during the period of 14 days prior and 14 days after the subject being administered anesthesia. The device 100 described above, or any other suitable device, can be used to provide the odor-rich environment.

The device and methods described herein may be used to provide enriched stimulation (ES) for patients and may stimulate patient brain function to assist in reducing, preventing, and/or treating POCD and/or POD and/or to reduce pain. In one implementation, a pair of devices (i.e., two devices) may be given to a patient during his or her preoperative visit to the pre-admission office. The two devices may have a direct voice/video call function to one another.

In some implementations, audio simulation, video simulation, and/or intellectual stimulation can also be administered to the subject to further assist in reducing, preventing, and/or treating POD, POCD, and/or postoperative pain. The audio stimulation, video stimulation, and/or intellectual stimulation can include enabling a patient to listen to music, watch movies, view photos, play a calculation game, or the like, or any combination thereof. The audio and video stimulation can further include communication with family members, doctors, nurses, and/or other persons. In some implementations, the device administering the odor-rich environment, includes the display, speaker, communication element, etc. can be used to provide the audio and video stimulation.

The Examples described below are intended to illustrate certain aspects of the invention to one of ordinary skill in the art and should not be interpreted as limiting the scope of the invention set forth in the claims.

Experimental Setup

To show that odor-enrichment can assist in reducing or preventing POD, POCD, and/or pain, three studies were performed: a control study, an interventional study, and an incisional study.

In both studies, four-month old female mice were housed in a controlled environment for seven days prior to being exposed to the procedures described below. The environment had an ambient temperature of about 20-22° C. and about 12 hours of light/dark on a reversed light cycle. Female mice were employed because olfactory impairment and Alzheimer's disease dementia occur more frequently in female patients.

In the interventional group, twenty mice were assigned to an odor-enrichment group and ten mice were assigned to a control group. The mice in the odor-enrichment group were exposed to two different fragrances which were placed in a cassette hanging from the cover of standard breeding cages for 24 hours daily for 21 days. Although not intended to be limiting, common fragrances used in the experiments on each day are listed in Table 1 below:

TABLE 1

| Day | Odorants |
|---|---|
| 1 | Rose, peppermint |
| 2 | Vanilla, ketchup |
| 3 | Yeast extract, coffee |
| 4 | Onion, dried fungus |
| 5 | Soy sauce, strawberry |
| 6 | Ginger, pu-erh tea |
| 7 | Cumin, honey |
| 8 | Olive oil, chocolate |
| 9 | Shrimp, sausage |
| 10 | Cucumber, apple |
| 11 | Tomato, banana |
| 12 | Celery, walnut |
| 13 | Garlic, cinnamon |
| 14 | Date, white pepper |
| 15 | Sweet potato, peppercorn oil |
| 16 | Caraway, vinegar |
| 17 | Kiwi, shallot |
| 18 | Brown sugar, grape |
| 19 | Pear, curry |
| 20 | Eggplant, fig |
| 21 | Carrot, leak |

The mice in the control group were treated with the same conditions as the mice in the odor-enrichment group, except the cassette did not contain any odorants. All mice were allowed access to food and water ad libitum.

In both studies, the mice in either the control group or the odor-enrichment group were further randomly assigned to an anesthesia/surgery group or a sham group. In the intervention study, this was done after the mice in the odor-enrichment group were exposed to the odor-enrichment for 21 days.

For the mice in the anesthesia/surgery group, anesthesia was induced and maintained with about 1.4% isoflurane in about 100% oxygen in a transparent acrylic chamber ("anesthesia chamber"). Fifteen minutes after anesthesia was induced, the mice were removed from the anesthesia chamber and anesthesia was maintained via a cone device. A longitudinal midline incision was made from the xiphoid to the 0.5 centimeter proximal pubic symphysis on the skin, abdominal muscles, and peritoneum. Then, the incision was sutured layer by layer with 5-0 Vicryl thread. At the end of the procedure, EMLA cream (2.5% lidocaine and 2.5% prilocaine) was applied to the incision wound.

The procedure for each mouse lasted approximately ten minutes. After the procedure, each mouse was placed back in the anesthesia chamber for up to two hours to receive the rest of the anesthesia of about 1.4% isoflurane in about 100% oxygen. After recovering from the anesthesia, the mice in the anesthesia/surgery group were returned to a home cage with food and water available ad libitum. EMLA cream was applied every eight hours for three days to treat the pain associated with the incision.

During the procedures on the anesthesia/surgery group of mice, the sham group mice were placed in a home cage with food and water available ad libitum with room air for about two hours, which is consistent with the condition of non-surgery in humans.

Example 1—Block Test

In both studies, two days prior to performing the procedure on the anesthesia/surgery group, each mouse was individually housed in a clean cage with five blocks for 24 hours. Each of the five blocks was labeled with a letter (A, B, C, D, and E). Each of the blocks then gained the scent of the mouse in the cage. Generally, the block test is used to access olfactory function, which determines the ability of the mice to discriminate between their own scent and that of other mice.

A baseline olfaction test was performed one day before the anesthesia/surgery procedure. Each mouse was habituated in the home cage for one hour prior to the test. Then, four of the five blocks with the scent of the mouse were placed in the middle of the home cage for about 30 seconds with one centimeter of space between each of the blocks. This procedure was repeated in three trials. On a fourth trial, the procedure was repeated, except one of the original blocks was replaced with a block containing the scent of another mouse ("a novel block"). The time the mouse sniffed the novel block was recorded by a camera. Olfactory impairment is defined when the mouse spends a reduced percentage of time to sniff the novel block.

Following the anesthesia/surgery procedure, the procedure was repeated at 1, 2, 3, and 11 days after the anesthesia surgery. As shown in FIGS. 10A-10C, in the control study, the mice in the anesthesia/surgery group sniffed the novel block for a significantly less amount of time than the mice in the sham group on days 1, 2, and 3 following the anesthesia/surgery or sham condition. The data suggests that anesthesia/surgery may impair short-term olfactory function in mice.

As shown in FIGS. 10D-10F, in the interventional study, the anesthesia/surgery did not significantly reduce the amount of time the mice sniffed the novel block as compared to sham condition. Thus, the results indicate that anesthesia/surgery did not induce olfactory impairment in the mice exposed to odor-enrichment for about 21 days.

Example 2—Barnes Maze Test

A Barnes maze is a circular open platform (having a diameter of about 90 centimeters) with 20 equally spaced holes. One of these holes connects with an escape box, which is a small, dark recessed chamber. A video camera hangs above the platform to record activity occurring on the platform. The Barnes maze was surrounded by a dark curtain with 4 simple colored-paper shapes (square, circle, triangle and star) as markers. The Barnes maze was located in a quiet area.

In both studies, the Barnes maze test consisted of three phases: habituation (day 6 after the anesthesia/surgery), spatial learning (training days, day 7 to 10 after the anesthesia/surgery), and spatial memory (testing day, day 11 after the anesthesia/surgery). Before starting each experiment, mice were acclimated to the testing room for 1 hour. On the habituation day, each of the mice was placed directly in the escape box for 2 minutes, then was allowed to enter the escape box through the hole and remained there for 4 minutes. Finally, each mouse was placed in a cylindrical black start chamber in the middle of the maze for 10 seconds. Then, the chamber was lifted and the mouse was motivated to escape by the stimulation of bright light (200 watt) and aversive noise from a buzzer (85 dB), gently guiding the mouse to the escape box. Immediately after the mouse entered the escape box, the buzzer and the light were turned off. Each mouse was allowed to remain in the escape box for 1 minute before being returned to the holding cage.

In the training days, each of the mice was subjected to the Barnes maze to test their spatial learning with 3 minutes per trial, 2 trials per day, and 15 minutes between each trial.

Each time, the mouse was placed under a cylindrical black start chamber in the center of the circular platform for 10 seconds, and was motivated to escape by the stimulation of the bright light and aversive noise. Once entering into the escape hole, the buzzer and the light were turned off and the mouse was allowed to remain in the escape box for 1 minute. If the mouse did not enter the escape box within 3 minutes, the mouse would be gently guided to the escape box and left the mouse inside the escape box for 1 minute. During the training days, the latency of the mouse to identify and enter the escape box was recorded.

On the testing day (day 11 after the anesthesia/surgery), the procedure was repeated except only one trial was performed. The latency to find the escape box, the number of wrong holes searched by the mouse before identifying and entering the escape box and time spent in target zone (the quarter of the Barnes maze platform containing the escape box) were recorded. The increase in latency to identify and enter the escape box, the increase in the number of wrong holes, and the reduction in time spent in target zone indicated cognitive impairment of the mice.

Figure 11A:
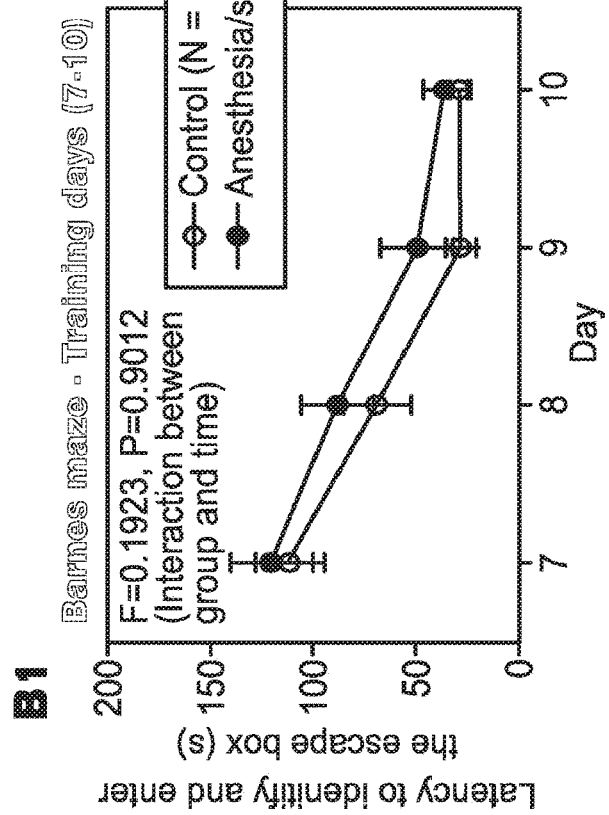
FIG. 11A is a graph of experimental results for a Barnes maze test from a control study according to some aspects of the present disclosure.
Figure 11D:
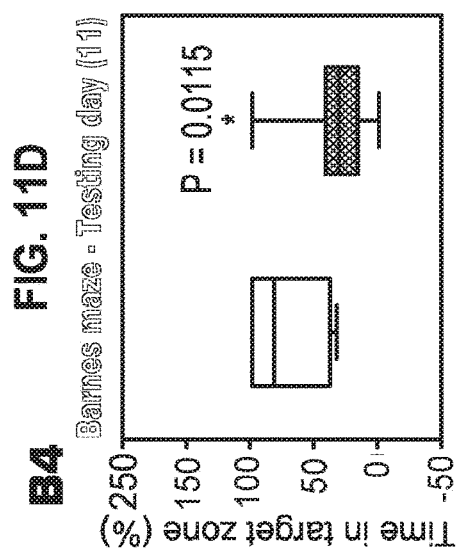
FIG. 11D is yet another graph of experimental results for the Barnes maze test of FIG. 11A.
Figure 11C:
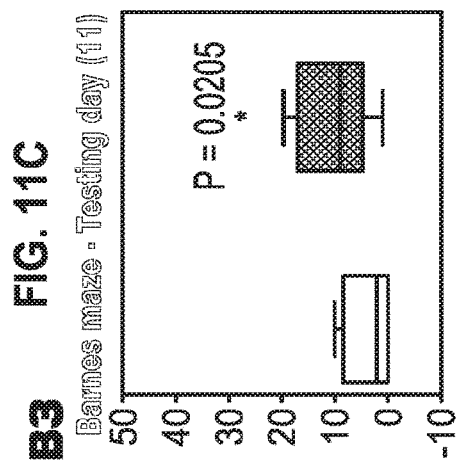
FIG. 11C is another graph of experimental results for the Barnes maze test of FIG. 11A.
Figure 11B:
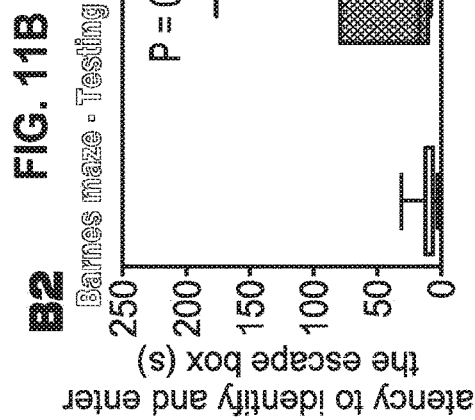
FIG. 11B is a graph of experimental results for the Barnes maze test of FIG. 11A.

As shown in FIG. 11A, during the training phase, in the control study, the mice in the anesthesia/surgery group showed no significant difference with respect to identifying and entering the escape box (escape latency) as compared to the mice that received the control condition (open circle). There was no significant correlation of treatment (control condition and anesthesia/surgery) and times (days) and the escape latency. As shown in FIG. 11B, anesthesia/surgery (black bar) significantly increased the latency in identifying and entering the escape box of the Barnes maze as compared to the control condition (white bar) at the testing day (about 11 days after the anesthesia/surgery) in the mice. As shown in FIG. 11C, anesthesia/surgery (black bar) significantly increased the amount of wrong holes the mice searched before identifying and entering the escape box as compared to the control condition (white bar) at the testing day (about 11 days after the anesthesia/surgery). As shown in FIG. 11D, anesthesia/surgery (black bar) significantly decreased the time the mice spent in the target zone (containing escape box) of the Barnes maze as compared to the control condition (white bar) at the testing day (about 11 days after the anesthesia/surgery).

Referring to FIGS. 12A-12D, in the interventional (odor-enrichment) study, the anesthesia/surgery did not significantly reduce the time the mice sniffed the novel block, as compared to the control condition. As shown in FIG. 12A, during the training phase, there was no significant correlation between treatment (control condition and anesthesia/surgery) and times (days) and the escape latency for the mice to identify and enter the target box (escape latency). As shown in FIG. 12B, following the odor enrichment, the anesthesia/surgery (black bar) did not significantly change the latency of the mice in the anesthesia/surgery group in identifying and entering the target box in Barnes maze test as compared to the control condition about 11 days after the anesthesia/surgery. As shown in FIG. 12C, following exposure to the odor-rich enrichment, the anesthesia/surgery (black bar) did not significantly increase the amount of wrong holes the mice in the anesthesia/surgery group searched before identifying and entering the escape box as compared to the control condition (white bar) about 11 days after the anesthesia/surgery. Referring to FIG. 12D, following exposure to the odor-rich enrichment, the anesthesia/surgery (black bar) did not significantly decrease the time the mice in the anesthesia/surgery spent in the target zone (containing the escape box) in the Barnes maze test as compared to the control condition (white bar) about 11 days after the anesthesia/surgery.

Example 3

Figure 13:
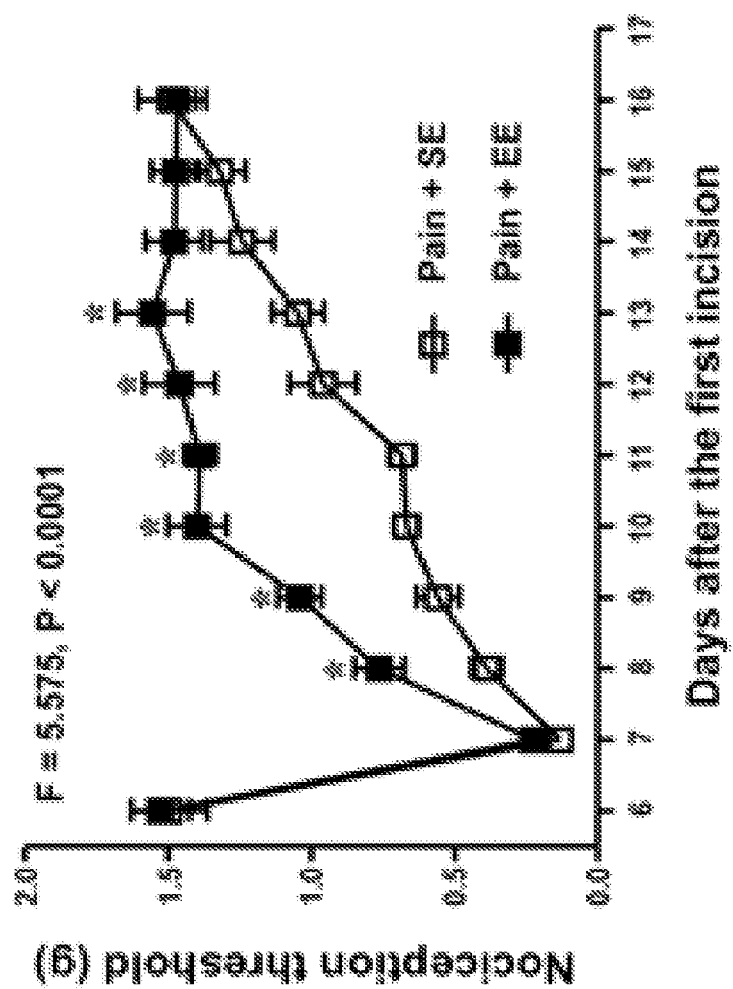
FIG. 13 is a graph of experimental results for an incisional pain test according to some aspects of the present disclosure.

In another study (the incision study), an incision was made in the feet of the about 5-8 month-old C57BL/6J mice under brief (about 3 minutes) exposure to about 1.4% isoflurane. The mice in a standard environment (SE) group stayed in the home cage. The mice in an enriched environment (EE) group stayed in a cage with color toys, which generated visual stimulation, for about two hours each day. The nociception threshold in each of the mice was determined by using the methods of nylon von Frey filaments up to 16 days after the incision. As shown in FIG. 13, enriched environment generally attenuated the incisional pain in mice as compared to standard environment.

While the present invention has been described with reference to one or more particular embodiments, those skilled in the art will recognize that many changes may be made thereto without departing from the spirit and scope of the present invention. Each of these embodiments and obvious variations thereof fall within the spirit and scope of the invention. Additional embodiments according to aspects of the present invention can combine any number of features from any of the embodiments described herein.

The invention claimed is:

1. A device for selectively providing an odor-rich environment, the device comprising:
   a housing including a central cavity and a plurality of chambers arranged around the periphery of the central cavity, each of the plurality of chambers being configured to store a predefined fragrance therein and having a respective outlet formed on an outer wall of the housing;
   a cover including an exterior surface having a top portion and an exterior sidewall, the cover further including at least one interior sidewall, the at least one exterior sidewall and at least one interior side wall forming an outer chamber therebetween, the at least one interior sidewall forming a generally central inner chamber therebetween, the cover including at least one vent formed on the exterior surface, the outer chamber being configured to slidably engage the housing such that the cover is configured to move between an open position and a closed position;
   a base disposed within the inner chamber of the cover;
   a push-push mechanism positioned within the inner chamber between the top portion of the cover and the base, the push-push mechanism being configured to transition the cover between the open position and the closed position in response to application of force to the top portion of the cover or the base; and
   at least one fragrance housed in at least one of the plurality of chambers, wherein responsive to the cover being in the open position, the fragrance is emitted through the at least one vent and at least one respective outlet;
   wherein (i) responsive to the cover being in the open position, the at least one vent is generally adjacent to the outlet of at least one of the plurality of chambers of the housing, and (ii) responsive to the cover being in the closed position, the exterior surface of the housing is generally adjacent to the respective outlet of at least one of the plurality of chambers of the housing.

2. The device of claim 1, wherein responsive to the cover being in the closed position, the cover substantially overlaps each respective outlet of the plurality of chambers of the housing to aid in inhibiting fluid communication between the plurality of chambers and an exterior of the device.

3. The device of claim 1, wherein the cover is configured to be rotated relative to the housing such that a preselected at least one fragrance is emitted from at least one of the plurality of chambers.

4. The device of claim 3, wherein (i) the plurality of chambers of the housing includes at least nine chambers and (ii) the at least one vent is at least three vents such that a rotated position of the cover relative to the housing causes one of at least six predefined fragrance combinations to be emitted from the device via the at least three vents.

5. The device of claim 1, wherein the at least one fragrance includes rose, peppermint, vanilla, ketchup, yeast extract, coffee, onion, dried fungus, soy sauce, strawberry, ginger, pu-erh tea, cumin, honey, olive oil, chocolate, shrimp, sausage, cucumber, apple, tomato, banana, celery, walnut, garlic, cinnamon, date, white pepper, sweet potato, peppercorn oil, caraway, vinegar, kiwi, shallot, brown sugar, grape, pear, curry, eggplant, fig, carrot, leek, or any combination thereof.

6. The device of claim 1, wherein the at least one vent includes a plurality of vents that are evenly spaced relative to one another on the exterior surface of the cover to aid in radially distributing the predefined fragrance from at least one of the plurality of chambers.

7. The device of claim 1, wherein the push-push mechanism includes a cam, a cam follower, a push rod, and a biasing spring, the cam being coupled to and extending from one of the top portion of the cover or the base to a pivot point positioned on the other of the top portion of the cover and the base, the cam having a cam path, wherein the cam follower is configured to be disposed within the cam path, the push rod having a first end coupled to the cam follower and a second end coupled to the pivot point, the biasing spring being configured to aid in maintaining the cover in either the open position or the closed position.

8. The device of claim 1, wherein the cover includes a plurality of apertures arranged on a top portion of the cover and a plurality of lights, each of the plurality of lights being visible through the plurality of apertures.

9. A method for selectively providing an odor rich environment, comprising:
providing a device including:
a housing, the housing including a central cavity and a plurality of chambers arranged around the periphery of the central cavity, each of the plurality of chambers having a respective outlet formed on an outer wall of the housing, at least one fragrance being housed within at least one of the plurality of chambers of the housing,
a cover, the cover including an exterior surface having a top portion, an exterior sidewall, and an interior sidewall, the exterior sidewall and the interior side wall forming an outer chamber therebetween, the interior sidewall forming a generally central inner chamber therebetween, the cover including at least one vent formed on the exterior surface, the outer chamber being configured to slidably engage the housing,
a base disposed within the inner chamber of the cover, and
a push-push mechanism positioned within the inner chamber between the top portion of the the base, the push-push mechanism being configured to transition the cover between an open position and a closed position in response to application of force to the top portion of the cover or the base; and
causing the cover to move to the open position such that the at least one vent is generally adjacent to the respective outlet of at least one of the plurality of chambers of the housing, thereby causing the at least one fragrance of at least one of the plurality of chambers to be emitted through the at least one vent and at least one respective outlet.

10. The method of claim 9, further comprising moving the cover to the closed position such that the exterior surface of the housing is generally adjacent to the respective outlet of at least one of the plurality of chambers of the housing.

11. The method of claim 10, further comprising, subsequent to moving the cover to the open position, rotating the cover relative to the housing such that a preselected at least one fragrance is emitted from the at least one vent and at least one respective outlet.

12. A device for selectively providing an odor-rich environment, the device comprising:
a housing including a central cavity and a plurality of chambers arranged around the periphery of the central cavity, each of the plurality of chambers being configured to store a predefined fragrance therein and having a respective outlet formed on an outer wall of the housing; and
a cover including an exterior surface having a top portion and an exterior sidewall, the cover further including at least one interior sidewall, the at least one exterior sidewall and at least one interior side wall forming an outer chamber therebetween, the at least one interior sidewall forming a generally central inner chamber therebetween, the cover including at least one vent formed on the exterior surface, the outer chamber being configured to slidably engage the housing such that the cover is configured to move between an open position and a closed position, the cover further including a plurality of apertures arranged on a top portion of the cover and a plurality of lights, each of the plurality of lights being visible through the plurality of apertures;
wherein (i) responsive to the cover being in the open position, the at least one vent is generally adjacent to the outlet of at least one of the plurality of chambers of the housing, and (ii) responsive to the cover being in the closed position, the exterior surface of the housing is generally adjacent to the respective outlet of at least one of the plurality of chambers of the housing.

13. The device of claim 12, wherein responsive to the cover being in the closed position, the cover substantially overlaps each respective outlet of the plurality of chambers of the housing to aid in inhibiting fluid communication between the plurality of chambers and an exterior of the device.

14. The device of claim 12, further comprising at least one fragrance housed in at least one of the plurality of chambers, wherein responsive to the cover being in the open position, the fragrance is emitted through the at least one vent and at least one respective outlet.

15. The device of claim 14, wherein the cover is configured to be rotated relative to the housing such that a preselected at least one fragrance is emitted from at least one of the plurality of chambers.

16. The device of claim 15, wherein (i) the plurality of chambers of the housing includes at least nine chambers and (ii) the at least one vent is at least three vents such that a rotated position of the cover relative to the housing causes one of at least six predefined fragrance combinations to be emitted from the device via the at least three vents.

17. The device of claim 14, wherein the at least one fragrance includes rose, peppermint, vanilla, ketchup, yeast extract, coffee, onion, dried fungus, soy sauce, strawberry, ginger, pu-erh tea, cumin, honey, olive oil, chocolate, shrimp, sausage, cucumber, apple, tomato, banana, celery, walnut, garlic, cinnamon, date, white pepper, sweet potato, peppercorn oil, caraway, vinegar, kiwi, shallot, brown sugar, grape, pear, curry, eggplant, fig, carrot, leek, or any combination thereof.

18. The device of claim 12, wherein the at least one vent includes a plurality of vents that are evenly spaced relative to one another on the exterior surface of the cover to aid in radially distributing the predefined fragrance from at least one of the plurality of chambers.

\* \* \* \* \*